(12) United States Patent
Yokoyama et al.

(10) Patent No.: US 11,080,888 B2
(45) Date of Patent: Aug. 3, 2021

(54) INFORMATION PROCESSING DEVICE AND INFORMATION PROCESSING METHOD

(71) Applicant: SONY CORPORATION, Tokyo (JP)

(72) Inventors: Masayuki Yokoyama, Tokyo (JP); Naoki Ide, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/491,079

(22) PCT Filed: Mar. 23, 2018

(86) PCT No.: PCT/JP2018/011827
§ 371 (c)(1),
(2) Date: Sep. 4, 2019

(87) PCT Pub. No.: WO2018/220963
PCT Pub. Date: Dec. 6, 2018

(65) Prior Publication Data
US 2020/0098136 A1    Mar. 26, 2020

(30) Foreign Application Priority Data

Jun. 2, 2017    (JP) .............................. JP2017-110199

(51) Int. Cl.
*G06T 7/00*    (2017.01)
*G06T 7/73*    (2017.01)
*G06F 3/01*    (2006.01)

(52) U.S. Cl.
CPC ................ *G06T 7/74* (2017.01); *G06F 3/013* (2013.01); *G06T 2207/10012* (2013.01); *G06T 2207/30201* (2013.01)

(58) Field of Classification Search
CPC ............. G06T 7/74; G06T 2207/10012; G06T 2207/30201; G06F 3/013
USPC ......................................................... 382/103
See application file for complete search history.

(56) References Cited

U.S. PATENT DOCUMENTS

| 2003/0169907 | A1 | 9/2003 | Edwards et al. |
| 2007/0025598 | A1* | 2/2007 | Kobayashi ........... G06K 9/0061 382/117 |
| 2010/0074477 | A1 | 3/2010 | Fujii et al. |
| 2017/0091520 | A1 | 3/2017 | Ishii et al. |

FOREIGN PATENT DOCUMENTS

| CN | 101517615 A | 8/2009 |
| EP | 2081152 A1 | 7/2009 |
| EP | 3151166 A1 | 4/2017 |
| JP | 2004-005167 A | 1/2004 |

(Continued)

OTHER PUBLICATIONS

International Search Report and Written Opinion of PCT Application No. PCT/JP2018/011827, dated Apr. 24, 2018, 09 pages of ISRWO.

*Primary Examiner* — Michael R Neff
(74) *Attorney, Agent, or Firm* — Chip Law Group

(57) ABSTRACT

To enable a more accurate estimation of the center of a pupil even in a situation in which it is difficult to capture an image of the entire pupil. An information processing device includes: an acquisition unit that acquires information regarding an iris in an eyeball; and an estimation unit that estimates a center position of a pupil in the eyeball on the basis of the information regarding the iris.

17 Claims, 14 Drawing Sheets

(56) References Cited

FOREIGN PATENT DOCUMENTS

| | | |
|---|---|---|
| JP | 2004-504684 A | 2/2004 |
| JP | 2005-304544 A | 11/2005 |
| JP | 2008-090482 A | 4/2008 |
| JP | 2017-068615 A | 4/2017 |
| WO | 2002/009025 A1 | 1/2002 |
| WO | 2008/041414 A1 | 4/2008 |

* cited by examiner

FIG. 12A   IRIS TEMPLATE
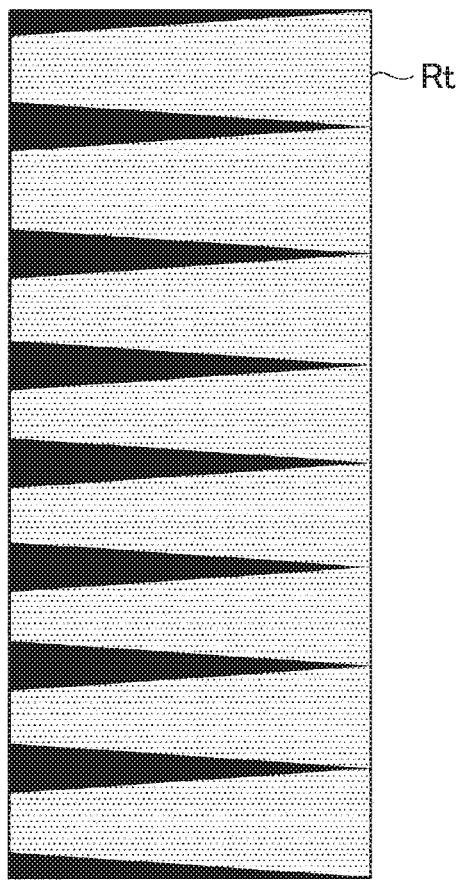
FIG. 12B   IRIS CANDIDATE REGION
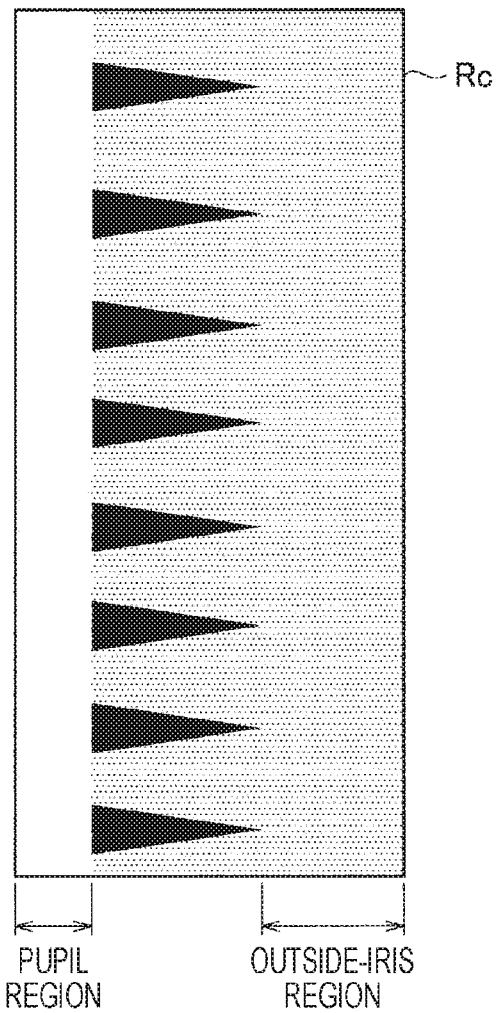
PUPIL REGION    OUTSIDE-IRIS REGION

FIG. 14A  BRIGHTNESS IMAGE

FIG. 14B  ρ DIRECTION INTEGRAL IMAGE

INFORMATION PROCESSING DEVICE AND INFORMATION PROCESSING METHOD

CROSS REFERENCE TO RELATED APPLICATIONS

This application is a U.S. National Phase of International Patent Application No. PCT/JP2018/011827 filed on Mar. 23, 2018, which claims priority benefit of Japanese Patent Application No. JP 2017-110199 filed in the Japan Patent Office on Jun. 2, 2017. Each of the above-referenced applications is hereby incorporated herein by reference in its entirety.

TECHNICAL FIELD

The present disclosure relates to an information processing device, an information processing method, and a program.

BACKGROUND ART

In recent years, various technologies in which a gaze of a user is detected and the detected gaze is used to control an operation of various information processing devices such as a smartphone, a wearable device, and the like have been suggested.

A method for detecting a gaze of a user can include, for example, a method in which an image of an eyeball of the user is captured by an image capturing unit such as a camera, and a position of a pupil is detected from the captured image to thereby estimate the gaze of the user. As a specific example, Patent Document 1 discloses an example of a technology of estimating a direction (hereinafter, referred to as a "gaze direction" or simply referred to as a "gaze") in which a gaze of a user is directed on the basis of a positional relation between a Purkinje image obtained by irradiating an eyeball of the user with infrared (IR) light, and the center of a pupil.

CITATION LIST

Patent Document

Patent Document 1: Japanese Patent Application Laid-Open No. 2015-13031

SUMMARY OF THE INVENTION

Problems to be Solved by the Invention

However, since an eyeball of a user is at least partially covered by an eyelid, even in a case where an image of the eyeball is captured by the image capturing unit, it is not always possible to capture an image of the entire pupil. Therefore, for example, in a situation in which the pupil is partially covered by the eyelid (in other words, in a situation in which an image of the entire pupil is not captured), it is difficult to accurately estimate the center of the pupil, and as a result, an error occurs in a detection result of the gaze direction in some cases.

In this regard, the present disclosure suggests an information processing device, an information processing method, and a program which can more accurately estimate the center of a pupil even in a situation in which it is difficult to capture an image of the entire pupil.

Solutions to Problems

According to the present disclosure, an information processing device including: an acquisition unit which acquires information regarding an iris in an eyeball; and an estimation unit which estimates a center position of a pupil in the eyeball on the basis of the information regarding the iris, is provided.

Furthermore, according to the present disclosure, an information processing method including: acquiring, by a computer, information regarding an iris in an eyeball; and estimating, by the computer, a center position of a pupil in the eyeball on the basis of the information regarding the iris, is provided.

According to the present disclosure, a program causing a computer to execute: acquiring information regarding an iris in an eyeball; and estimating a center position of a pupil in the eyeball on the basis of the information regarding the iris, is provided.

Effects of the Invention

According to the present disclosure described above, provided are the information processing device, the information processing method, and the program which can more accurately estimate the center of a pupil even in a situation in which it is difficult to capture an image of the entire pupil.

Note that effects of the present disclosure are not necessarily limited to the effects described above, and, along with or instead of the effects described above, any of the effects shown in the present specification, or other effects that can be grasped from the present specification may be achieved.

BRIEF DESCRIPTION OF DRAWINGS

FIGS. 12A and 12B are explanatory views for describing a processing relating to a comparison between polar coordinate images by an information processing device according to the embodiment.

MODE FOR CARRYING OUT THE INVENTION

Figure 1:
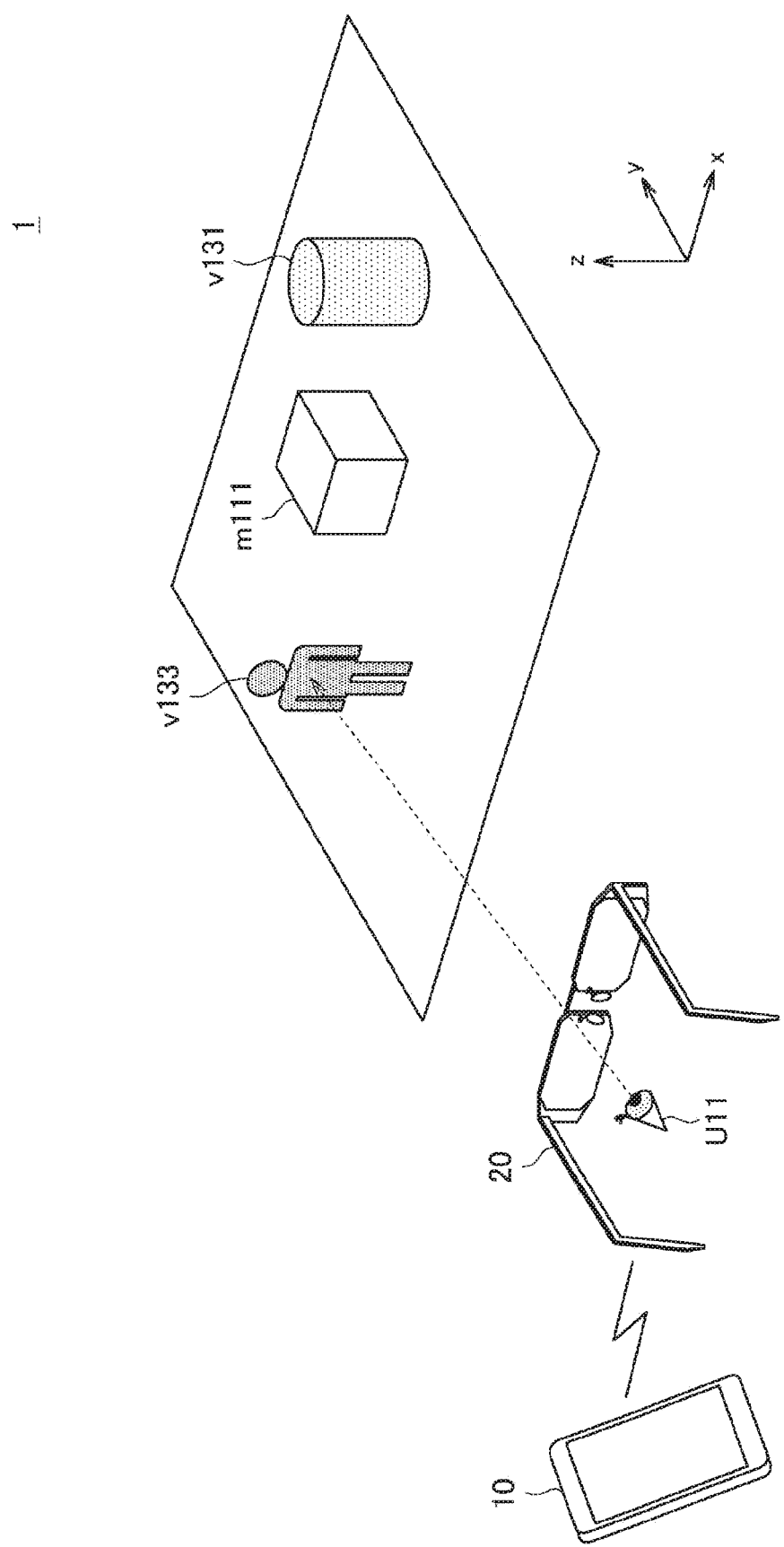
FIG. 1 is an explanatory view for describing an example of a schematic configuration of an information processing system according to an embodiment of the present disclosure.

Hereinafter, a preferred embodiment of the present disclosure will be described in detail with reference to the accompanying drawings. Note that in the present specification and the drawings, constituent elements having substantially the same functional configuration will be denoted by the same reference numerals, and redundant description will be omitted.

Note that descriptions will be provided in the following order.
1. Schematic Configuration
1.1 System Configuration
1.2. Configuration of Input and Output Device
2. Study on Gaze Detection
3. Technical Characteristics
3.1. Functional Configuration
3.2. Details of Processing Relating to Estimation of Center Position of Pupil
3.3. Modified Example
4. Example of Hardware Configuration
5. Conclusion <<1. Schematic Configuration>>
<1.1. System Configuration>

First, an example of a schematic configuration of an information processing system according to an embodiment of the present disclosure will be described with reference to FIG. 1. FIG. 1 is an explanatory view for describing the example of the schematic configuration of the information processing system according to the embodiment of the present disclosure, and illustrates an example of a case of presenting various contents to a user by using a so-called augmented reality (AR) technology.

In FIG. 1, Reference Sign m111 schematically indicates an object (for example, an actual object) positioned in an actual space. Furthermore, Reference Signs v131 and v133 schematically indicate virtual contents (for example, virtual objects) presented while being superimposed on the actual space. In other words, for example, an information processing system 1 according to the present embodiment superimposes a virtual object on an object such as the actual object m111 in an actual space to present the virtual object to the user on the basis of the AR technology. Note that both of the actual object and the virtual object are presented in FIG. 1 in order to facilitate understanding of characteristics of the information processing system according to the present embodiment.

As illustrated in FIG. 1, the information processing system 1 according to the present embodiment includes an information processing device 10 and an input and output device 20. The information processing device 10 and the input and output device 20 are configured to be able to transmit and receive information to and from each other through a predetermined network. Note that a type of network connecting the information processing device 10 and the input and output device 20 to each other is not particularly limited. As a specific example, the network may be constituted by a so-called wireless network such as a network based on a wireless fidelity (Wi-Fi) (registered trademark) protocol. Furthermore, as another example, the network may also be constituted by Internet, a dedicated line, a local area network (LAN), a wide area network (WAN), or the like. Furthermore, the network may include a plurality of networks and may also be at least partially configured as a wired network.

The input and output device 20 is a configuration for acquiring various input information and presenting various output information to a user holding the input and output device 20. Furthermore, the information processing device 10 controls the presentation of the output information performed by the input and output device 20 on the basis of the input information acquired by the input and output device 20. For example, the input and output device 20 acquires information (for example, a captured image of the actual space) for recognizing the actual object m111 as the input information, and outputs the acquired information to the information processing device 10. The information processing device 10 recognizes a position of the actual object m111 in the actual space on the basis of the information acquired from the input and output device 20, and presents the virtual objects v131 and v133 to the input and output device 20 on the basis of a recognition result. According to such a control, the input and output device 20 can present the virtual objects v131 and v133 to the user so that the virtual objects v131 and v133 are superimposed on the actual object m111 on the basis of the so-called AR technology.

Furthermore, the input and output device 20 is configured as, for example, a so-called head wearable device used by being mounted on at least a portion of a head of the user, and may also be configured to be able to acquire information for detecting or estimating a gaze of the user. For example, in the example in FIG. 1, the input and output device 20 may capture an image of an eyeball U11 of the user by an image capturing unit or the like, and acquire an image capturing result as the information for detecting the gaze of the user. With such a configuration, for example, the information processing device 10 can analyze the image of the eyeball U11 acquired by the input and output device 20 to detect the gaze of the user. Furthermore, in a case where it is recognized that the user gazes at a desired object (for example, the actual object m111, the virtual objects v131 and v133, and the like) on the basis of a result of detecting the gaze of the user, the information processing device 10 may specify the object as an operation target. Furthermore, the information processing device 10 may specify an object to which the gaze of the user is directed as an operation target in accordance with a predetermined operation with respect to the input and output device 20 as a trigger. In this manner, the information processing device 10 may specify the operation target and perform a processing associated with the operation target to provide various services to the user through the input and output device 20.

Note that the input and output device 20 and the information processing device 10 are devices different from each other in FIG. 1, but the input and output device 20 and the information processing device 10 may be configured integrally with each other. Furthermore, details of the configuration and processing of the input and output device 20 and the information processing device 10 will be separately described later. Furthermore, in the example illustrated in FIG. 1, a case where an eyeglasses-type wearable device is applied as the input and output device 20 has been described, but a configuration and an aspect of the device to which the technology according to the present disclosure is applied are not necessarily limited thereto. As a specific example, a terminal device configured to be portable, such as a smartphone or the like, may be applied as the input and output device 20.

Hereinabove, the example of the schematic configuration of the information processing system according to the embodiment of the present disclosure has been described with reference to FIG. 1.

<1.2. Configuration of Input and Output Device>

Figure 2:
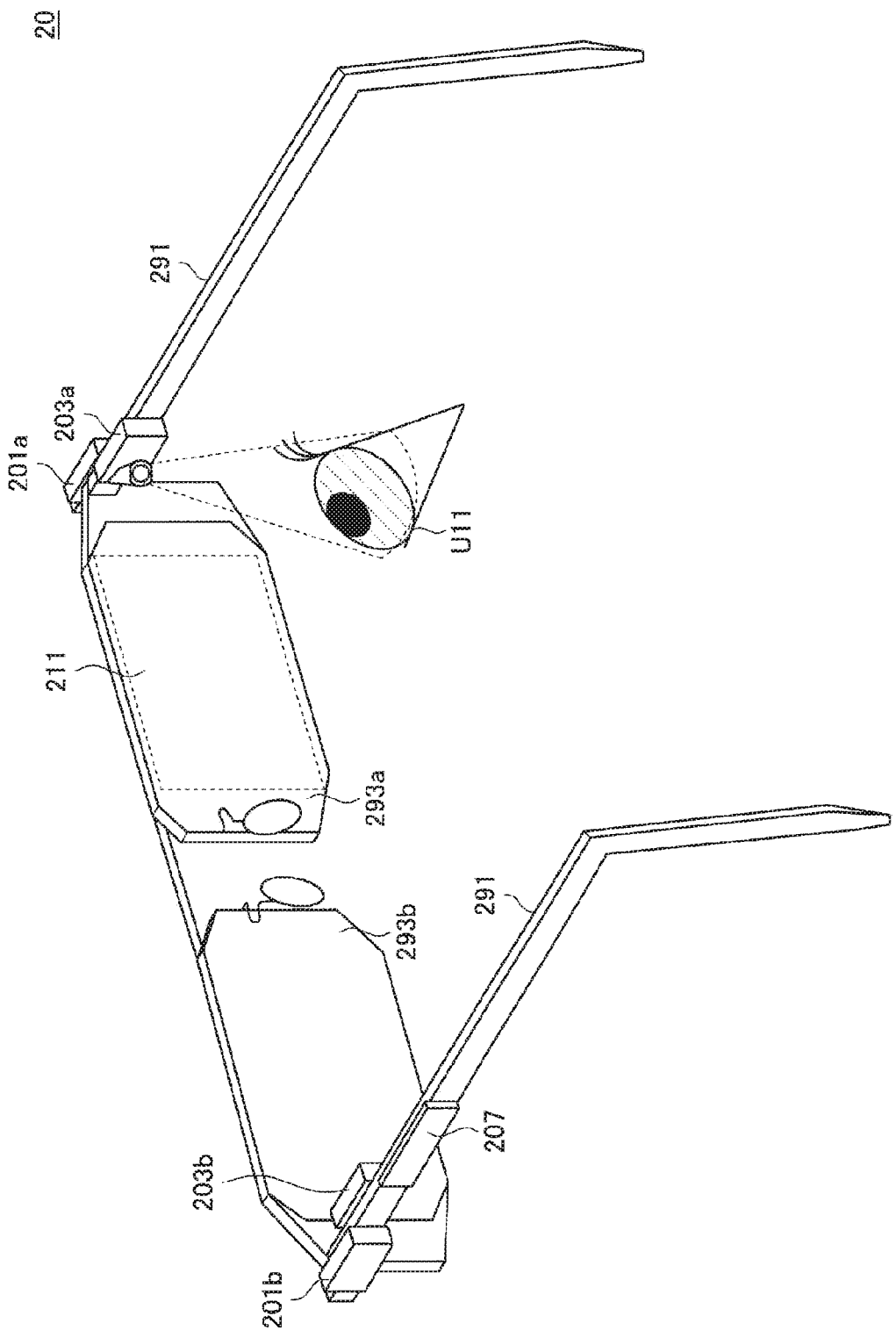
FIG. 2 is an explanatory view for describing an example of a schematic configuration of an input and output device according to the embodiment.

Next, an example of a schematic configuration of the input and output device 20 according to the present embodiment illustrated in FIG. 1 will be described with reference to FIG. 2. FIG. 2 is an explanatory view for describing the example of the schematic configuration of the input and output device according to the present embodiment.

As described above, the input and output device 20 according to the present embodiment can be configured as a so-called head-mounted device which is used by being mounted on at least a portion of the head of the user. For example, in the example illustrated in FIG. 2, the input and output device 20 is configured as a so-called eyewear (eyeglasses-type) device, and at least any one of a lens 293a or a lens 293b is configured as a transparent display (output unit 211). Furthermore, the input and output device 20 includes first image capturing units 201a and 201b, an operation unit 207, and holding units 291 corresponding to a frame of a glasses. Furthermore, the input and output device 20 may also include second image capturing units 203a and 203b. Note that hereinafter, various descriptions will be provided under the assumption that the input and output device 20 includes the second image capturing units 203a and 203b. The holding units 291 hold the output unit 211, the first image capturing units 201a and 201b, the second image capturing units 203a and 203b, and the operation unit 207 so that they have a predetermined positional relation with respect to the head of the user when the input and output device 20 is mounted on the head of the user. Furthermore, although not illustrated in FIG. 2, the input and output device 20 may include a voice collecting unit for collecting a voice of the user.

Here, a more specific configuration of the input and output device 20 will be described. For example, in the example illustrated in FIG. 2, the lens 293a corresponds to a lens for the right eye, and the lens 293b corresponds to a lens for the left eye. In other words, in a case where the input and output device 20 is mounted, the holding units 291 hold the output unit 211 so that the output unit 211 (in other words, the lenses 293a and 293b) is positioned in front of the user.

The first image capturing units 201a and 201b are configured as a so-called stereo camera, and when the input and output device 20 is mounted on the head of the user, the first image capturing units 201a and 201b are held by the holding units 291, respectively, so as to face a direction (in other words, in front of the user) in which the head of the user faces. At this time, the first image capturing unit 201a is held in the vicinity of the right eye of the user, and the first image capturing unit 201b is held in the vicinity of the left eye of the user. The first image capturing units 201a and 201b capture images of a subject (in other words, the actual object positioned in the actual space) positioned in front of the input and output device 20 at positions different from each other on the basis of such a configuration. As a result, the input and output device 20 can acquire the images of the subject positioned in front of the user, and calculate a distance from the input and output device 20 to the subject on the basis of parallax between the images captured by the first image capturing units 201a and 201b.

Note that as long as the distance between the input and output device 20 and the subject can be measured, a configuration or method thereof is not particularly limited. An a specific example, the distance between the input and output device 20 and the subject can be measured on the basis of a method such as a multi-camera stereo, moving parallax, time of flight (TOF), or structured light. Here, the TOF is a method in which light such as ultraviolet rays is projected to the subject and a time taken for the projected light to be reflected by the subject and return is measured for each pixel to thereby obtain an image (a so-called distance image) including a distance (depth) to the subject on the basis of a result of the measurement. Furthermore, the structured light is a method in which a pattern is projected to the subject by using light such as ultraviolet rays, and the projected pattern is captured to obtain a distance image including a distance (depth) to the subject on the basis of a change of the pattern obtained from a capturing result. Furthermore, the moving parallax is a method in which a distance to the subject is measured on the basis of parallax even in a so-called monocular camera. Specifically, the camera is moved to capture images of the subject at different points of views and a distance to the subject is measured on the basis of parallax between captured images. Note that at the time, various sensors recognize a moving distance and a moving direction of the camera, such that it is possible to measure a distance to the subject with high precision. Note that a configuration (for example, a monocular camera, a stereo camera, or the like) of the image capturing unit may be changed according to the distance measurement method.

Furthermore, the second image capturing units 203a and 203b are held by the holding units 291, respectively, so that eyeballs of the user are positioned within image capturing ranges, respectively, when the input and output device 20 is mounted on the head of the user. As a specific example, the second image capturing unit 203a is held so that the right eye of the user is positioned within the image capturing range. On the basis of such a configuration, it is possible to recognize a direction in which a gaze of the right eye is directed on the basis of an image of the eyeball (in other words, the eyeball U11 illustrated in FIG. 2) of the right eye captured by the second image capturing unit 203a, and a positional relation between the second image capturing unit 203a and the right eye. Similarly, the second image capturing unit 203b is held so that the left eye of the user is positioned within the image capturing range. In other words, it is possible to recognize a direction in which a gaze of the left eye is directed on the basis of an image of the eyeball of the left eye captured by the second image capturing unit 203b, and a positional relation between the second image capturing unit 203b and the left eye. Note that a configuration in which the input and output device 20 includes the second image capturing units 203a and 203b is illustrated in the example in FIG. 2, but only any one of the second image capturing units 203a and 203b may be provided.

The operation unit 207 is a configuration for receiving an operation from the user with respect to the input and output device 20. The operation unit 207 may be constituted by, for example, an input device such as a touch panel, a button, or the like. The operation unit 207 is held at a predetermined position in the input and output device 20 by the holding unit 291. For example, the operation unit 207 is held at a position corresponding to a temple of glasses in the example illustrated in FIG. 2.

Furthermore, the input and output device 20 according to the present embodiment may have a configuration in which, for example, an acceleration sensor and an angular velocity sensor (gyro sensor) are provided, such that a motion (in other words, a motion of the input and output device 20 itself) of the head of the user on which the input and output device 20 is mounted can be detected. As a specific example, the input and output device 20 may detect components in a yaw direction, a pitch direction, and a roll direction, respectively, as the motion of the head of the user to recognize a change in at least one of a position or a posture of the head of the user.

On the basis of such a configuration described above, the input and output device 20 according to the present embodiment can recognize a change in position or posture thereof in the actual space in accordance with the motion of the head of the user. Furthermore, at the time, the input and output device 20 can also present a virtual content (in other words, the virtual object) to the output unit 211 so that the content is superimposed on the actual object positioned in the actual space on the basis of the so-called AR technology. Note that an example of a method (in other words, self position estimation) for estimating, by the input and output device 20, a position and a posture of the input and output device 20 itself in the actual space will be separately described later in detail.

Note that an example of a head-mounted display (HMD) which can be applied as the input and output device 20 includes a see-through type HMD, a video see-through type HMD, and a retinal imaging type HMD.

As for the see-through type HMD, for example, a half mirror or a transparent light guide plate is used and a virtual image optical system including a transparent light guide unit or the like is held in front of eyes of a user to display an image on an inner side of the virtual image optical system. Therefore, the user wearing the see-through type HMD can see the outside scenery even while watching an image displayed on the inner side of the virtual image optical system. With such a configuration, the see-through type HMD can also superimpose an image of a virtual object on an optical image of an actual object positioned in an actual space according to a result of recognizing at least one of a position or a posture of the see-through type HMD on the basis of, for example, the AR technology. Note that a specific example of the see-through type HMD can include a so-called glasses-type wearable device in which a portion corresponding to a lens of glasses is configured as the virtual image optical system. For example, the input and output device 20 illustrated in FIG. 2 corresponds to an example of the see-through type HMD.

As for the video see-through type HMD, in a case where the video see-through type HMD is mounted on a head or a face of a user, the video see-through type HMD is mounted so as to cover eyes of the user, and a display unit such as a display is held in front of the eyes of the user. Furthermore, the video see-through type HMD includes an image capturing unit for capturing an image of surrounding scenery, and an image of scenery in front of the user is displayed on the display unit, the image being captured by the image capturing unit. With such a configuration, although it is difficult for the user wearing the video see-through type HMD to directly see the outside scenery, it is possible to check the outside scenery through the image displayed on the display unit. Furthermore, at this time, the video see-through type HMD can also superimpose a virtual object on an optical image of the outside scenery according to a result of recognizing at least one of a position or a posture of the video see-through type HMD on the basis of, for example, the AR technology.

As for the retinal imaging type HMD, a projecting unit is held in front of eyes of a user, and an image is projected onto the eyes of the user from the projecting unit so that the image is superimposed on the outside scenery. More specifically, in the retinal imaging type HMD, the image is directly projected from the projecting unit to retinas of the eyes of the user to form the image on the retinas. With such a configuration, even a nearsighted or farsighted user can watch a clearer image. Furthermore, the user wearing the retinal imaging type HMD can see the outside scenery even while watching an image projected from the projecting unit. With such a configuration, the retinal imaging type HMD can also superimpose an image of a virtual object on an optical image of an actual object positioned in an actual space according to a result of recognizing at least one of a position or a posture of the retinal imaging type HMD on the basis of, for example, the AR technology.

Furthermore, hereinabove, the example of the configuration of the input and output device 20 according to the present embodiment has been described under the premise that the AR technology is applied. However, the configuration of the input and output device 20 is not necessarily limited thereto. For example, in a case where it is presumed that a virtual reality (VR) technology is applied, the input and output device 20 according to the present embodiment may be configured as an HMD which is called an immersive HMD. The immersive HMD is mounted so as to cover eyes of a user, and a display unit such as a display is held in front of the eyes of the user, similarly to the video see-through type HMD. Therefore, it is difficult for the user wearing the immersive HMD to directly see the outside scenery (in other words, scenery of an actual world), and only an image displayed on the display unit comes into a visual field of the user. With such a configuration, the immersive HMD can give a sense of immersion to the user watching the image.

Hereinabove, the example of the schematic configuration of the input and output device according to the embodiment of the present disclosure has been described with reference to FIG. 2.

<2. Study on Gaze Detection>

Next, an outline of an example of a technology of detecting a gaze of a user will be described, and then a problem to be solved by the information processing system according to the embodiment of the present disclosure will be described.

A method for detecting (estimating) a gaze of a user can include, for example, a method in which an image of an eyeball of the user is captured by an image capturing unit such as a camera, and a position of a pupil is detected from the captured image to thereby estimate the gaze of the user. As a specific example, a technology of estimating a gaze direction of a user on the basis of a positional relation between a Purkinje image obtained by irradiating an eyeball of the user with infrared (IR) light, and the center of a pupil can be included.

More specifically, for example, Japanese Patent Application Laid-Open No. H06-304141 discloses a method of calculating a rotation angle θ of an optical axis of an eyeball from a distance of a distance xc between a central point (xd+xe)/2 of a plurality of Purkinje images in a captured image, and the center of a pupil, by using the Purkinje images in the captured image, obtained by corneal reflection of IR light to know a distance Loc between the center of curvature of the cornea and the center of the pupil in advance. Note that in the method, it is required that a coefficient A1 for correcting an individual difference in distance Loc, and a correction coefficient B1 for converting the rotation angle θ into an actual gaze angle (visual axis) θH are set in advance before detecting the gaze. Furthermore, Japanese Patent Application Laid-Open No. H09-28673 discloses a method of specifying a user by matching (iris authentication) with a registered iris pattern and selecting correction information held for each individual.

In a case where a position of a region including a pupil or an iris is used to estimate the gaze like the cornea reflection method described above, for example, the position of the pupil or iris region is estimated by image processing in some cases. Note that as a method for estimating the position of the pupil or the iris on the basis of the image processing, for example, a method of searching a region that highly matches an edge of a figure template such as a circle or an oval is often applied.

Figure 3:
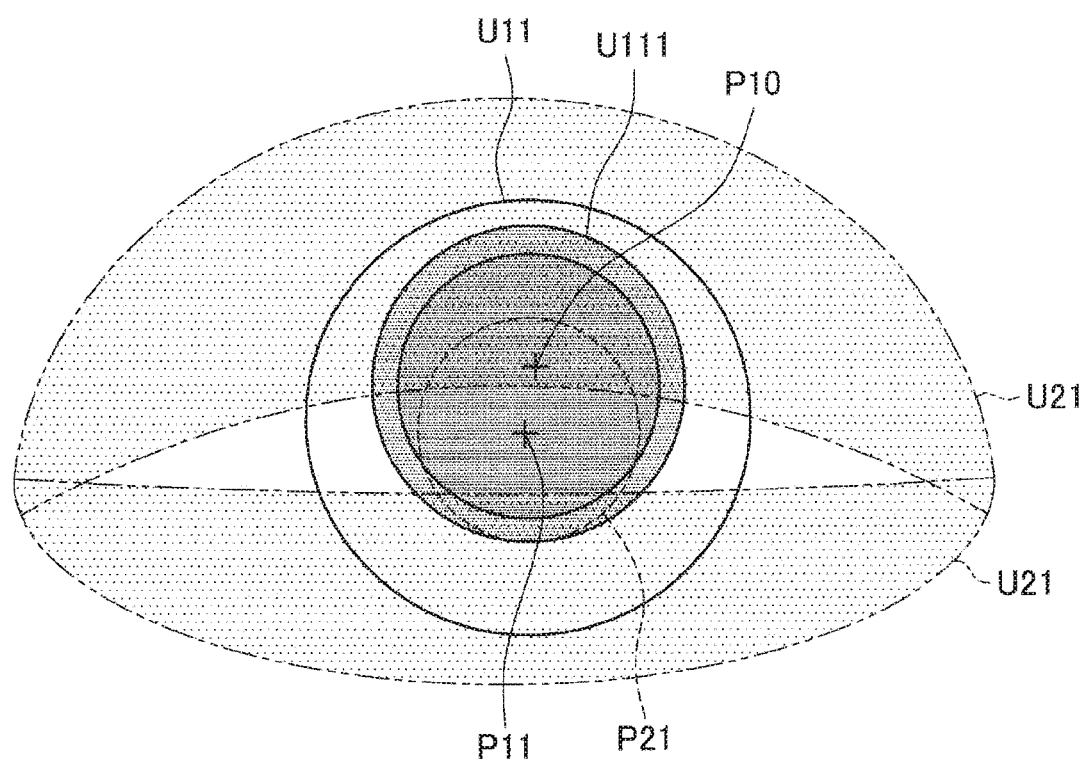
FIG. 3 is an explanatory view for describing an example of a processing relating to a pupil position estimation.

However, since an eyeball of a user is at least partially covered by an eyelid, even in a case where an image of the eyeball is captured by the image capturing unit, it is not always possible to capture an image of the entire pupil. For example, FIG. 3 is an explanatory view for describing an example of a processing relating to the pupil position estimation, and schematically illustrates a situation of a case where the eyeball U11 of the user is viewed from the front of the user. In FIG. 3, Reference Sign U111 schematically indicates a pupil of the eyeball U11 of the user. Furthermore, Reference Sign U21 schematically indicates an eyelid of the user. In other words, in the example illustrated in FIG. 3, the pupil U111 is partially covered by the eyelid U21.

In a state as illustrated in FIG. 3, in a case of estimating a position of the center of the pupil U111 on the basis of image processing, for example, a region indicated by Reference Sign P21 is estimated as a region of the pupil U111. Therefore, in this case, a center P11 of the region P21 is estimated as the center of the pupil U111. However, in the example illustrated in FIG. 3, the pupil U111 is partially covered by the eyelid U21, and thus the actual center is positioned at a position indicated by Reference Sign P10.

As such, in a situation in which the pupil is partially covered by the eyelid, it is difficult to capture an image of the entire pupil, and thus it is difficult to estimate an accurate position of the pupil in some cases. In such a case, it can be presumed that precision in gaze estimation will deteriorate. Furthermore, in the image of the eyeball captured by the image capturing unit, a contour (edge) of the pupil is blurred or a contrast with respect to the iris pattern is decreased in some cases. Even in such a case, it is difficult to estimate an accurate position of the pupil, and even precision in the gaze estimation deteriorates in some cases.

In consideration of such a situation, the present disclosure suggests an example of a technology which enables more accurate estimation of the center of the pupil even in a situation in which it is difficult to capture an image of the entire pupil as in the example described with reference to FIG. 3.

<3. Technical Characteristics>

Hereinafter, technical characteristics of the information processing system according to the present embodiment will be described.

<3.1. Functional Configuration>

Figure 4:
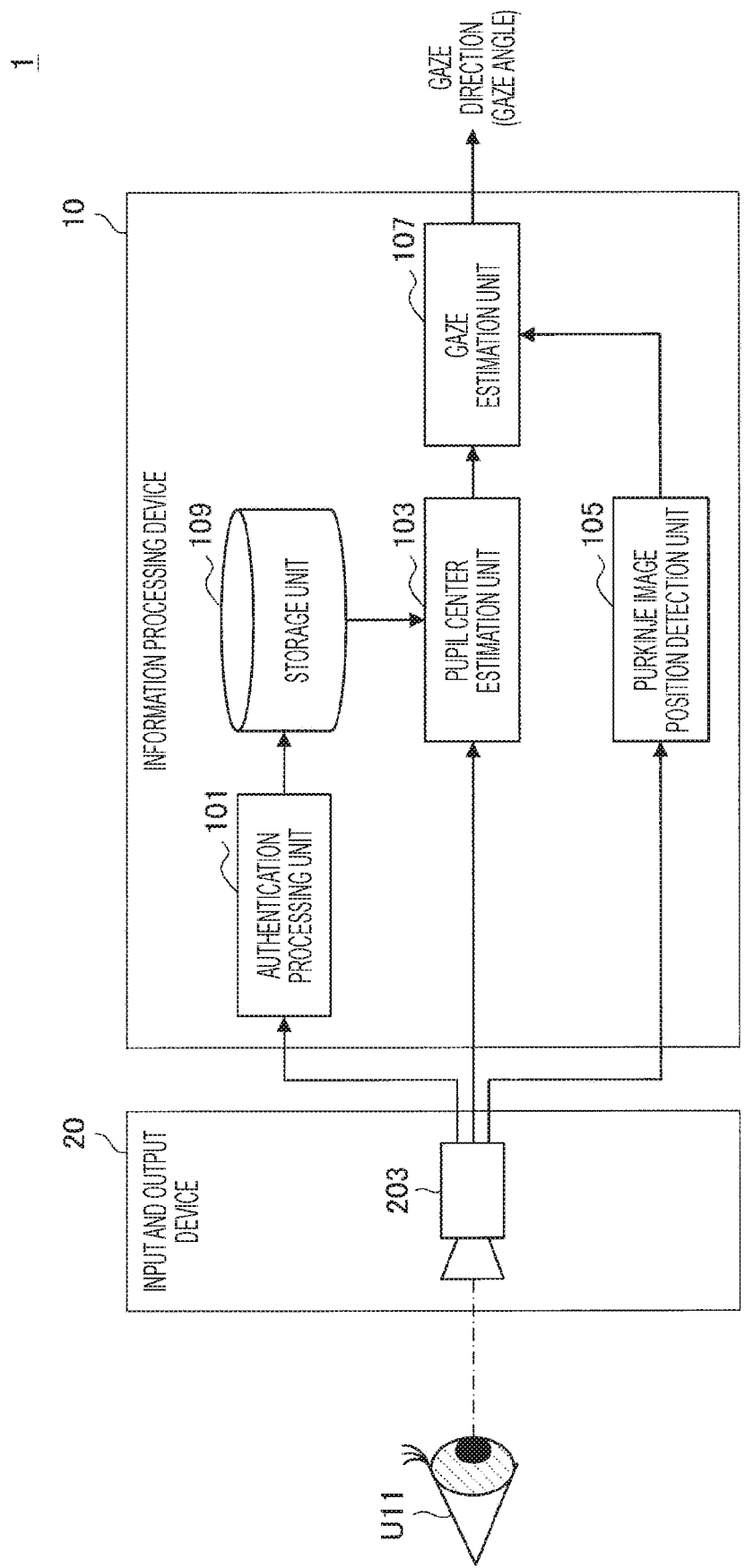
FIG. 4 is a block diagram illustrating an example of a functional configuration of the information processing system according to the embodiment.

First, an example of a functional configuration of the information processing system according to the present embodiment will be described with reference to FIG. 4, focusing particularly on the configuration of the information processing device 10 described with reference to FIG. 1. FIG. 4 is a block diagram illustrating an example of the functional configuration of the information processing system according to the present embodiment.

As described above with reference to FIG. 1, the information processing system 1 according to the present embodiment includes the information processing device 10 and the input and output device 20. Note that as for the input and output device 20, an image capturing unit 203 (corresponding to the second image capturing units 203a and 203b illustrated in FIG. 1) capturing an image of the eyeball U11 of the user is illustrated and other configurations are omitted in the example illustrated in FIG. 4. Furthermore, as for the information processing device 10, a configuration relating to estimation of a gaze of a user is illustrated and other configurations are omitted in the example illustrated in FIG. 4.

As illustrated in FIG. 4, the image capturing unit 203 captures an image of the eyeball U11 of the user and outputs the captured image to the information processing device 10. Note that a timing at which the image capturing unit 203 captures the image of the eyeball U11 is not particularly limited. As a specific example, the image capturing unit 203 may capture images of the eyeball U11 as a moving image to sequentially acquire the images of the eyeball U11. Furthermore, as another example, the image capturing unit 203 may capture the image of the eyeball U11 in accordance with a predetermined event as a trigger.

As illustrated in FIG. 4, the information processing device 10 includes an authentication processing unit 101, a pupil center estimation unit 103, a Purkinje image position detection unit 105, a gaze estimation unit 107, and a storage unit 109.

The storage unit 109 is a storage region for temporarily or constantly storing various data. For example, the image of the eyeball U11 captured by the image capturing unit 203 may be stored.

Figure 5:
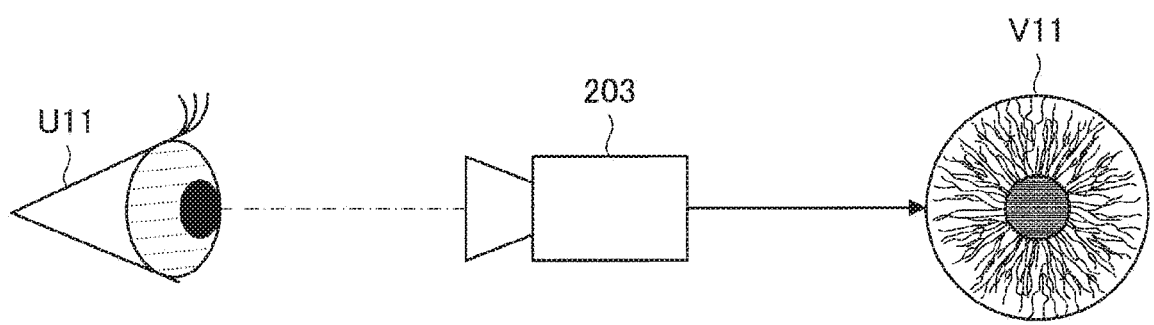
FIG. 5 is an explanatory view for describing an outline of a processing relating to iris authentication in the information processing system according to the embodiment.

The authentication processing unit 101 acquires, from the image capturing unit 203, the image of the eyeball U11 captured by the image capturing unit 203, and performs authentication of the user by using the iris pattern captured in the image. For example, FIG. 5 is an explanatory view for describing an outline of a processing relating to iris authentication in the information processing system according to the present embodiment. In FIG. 5, Reference Sign V11 illustrates an image of the eyeball U11 captured by the image capturing unit 203. The image V11 obtained by capturing an image of the pupil and the iris as illustrated in FIG. 5 is used for the iris authentication. In other words, the authentication processing unit 101 compares the image V11 captured by the image capturing unit 203 with another image (in other words, an image of the eyeball U11) stored in a predetermined storage region (for example, the storage unit 109) in advance, the image V11 and the another image each including the pupil and the iris as subjects, thereby performing authentication of the user.

Furthermore, the information processing device 10 according to the present embodiment uses a region of an iris pattern included in the image V11 of the eyeball U11 as a subject to estimate the center of the pupil (even to estimate a gaze), and details thereof will be described later. On the basis of such a characteristic, for example, the information processing device 10 uses the image V11 (specifically, the image including the region of the iris pattern) of the eyeball U11 used for the iris authentication as a template for estimation (even for gaze estimation) of the center of the pupil, in the example illustrated in FIG. 4. Therefore, the authentication processing unit 101 stores the image of the eyeball U11 used for the authentication as the template in the storage unit 109.

Note that in the information processing system 1 according to the present embodiment, although an image of the entire iris pattern may not necessarily be captured as the template, the wider the range of the captured image of the iris pattern is, the higher the precision in estimating the center of the pupil can become. Therefore, for example, the user may be urged to do a motion such as opening eyes wide so that a wider range of the image of the iris pattern is captured (ideally, so that an image of the entire iris pattern is captured) at the time of the iris authentication. Note that the template will also be referred to as "iris template" in the following description.

Figure 6:
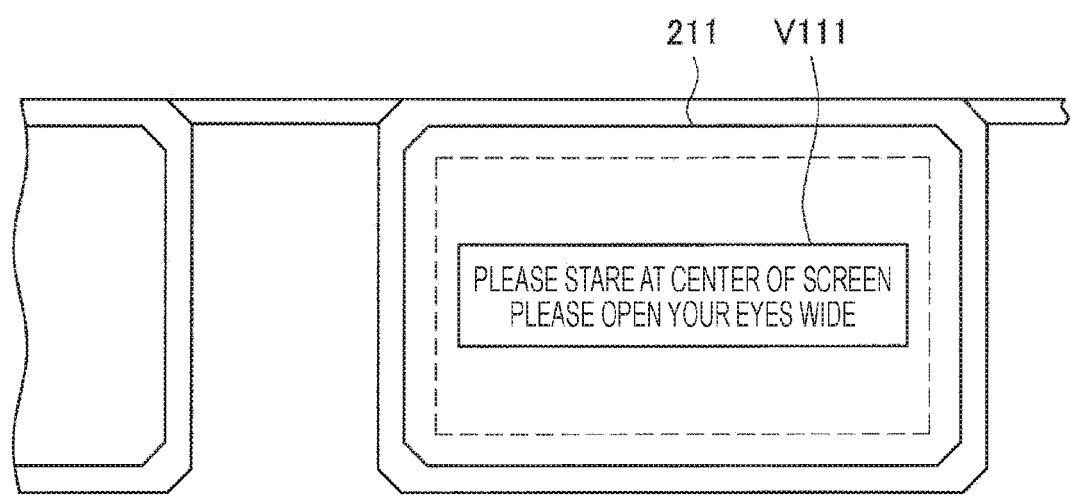
FIG. 6 is a view illustrating an example of a user interface of the iris authentication in the information processing system according to the embodiment.

For example, FIG. 6 is a view illustrating an example of a user interface of the iris authentication in the information processing system 1 according to the present embodiment. In the example illustrated in FIG. 6, notification information V111 for urging the user to do a motion of staring at the center of a screen and opening eyes wide is displayed on the output unit 211 of the input and output device 20 illustrated in FIG. 2, such that the image V11 of the eyeball U11 of the user is captured in a more suitable aspect.

Figure 7:
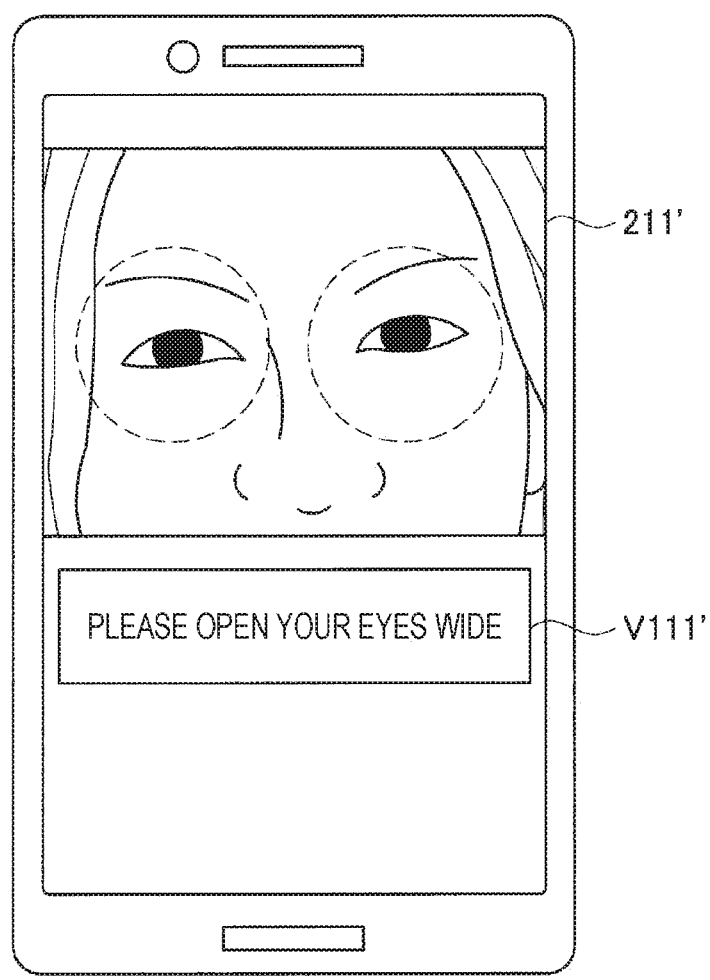
FIG. 7 is a view illustrating another example of the user interface of the iris authentication in the information processing system according to the embodiment.

Furthermore, FIG. 7 is a view illustrating another example of the user interface of the iris authentication in the information processing system 1 according to the present embodiment, and illustrates an example of a case in which a terminal device such as a smartphone or the like is used as the input and output device 20. In the example illustrated in FIG. 7, notification information V111' for urging the user to do a motion of opening eyes wide is displayed on an output unit 211' of the terminal device, such that the image V11 of the eyeball U11 of the user is captured in a more suitable state.

Furthermore, a partial image including the region of the iris in the image V11 of the eyeball U11 may be stored as the iris template in the storage unit 109. In this case, for example, a method such as an eye region segmentation is applied, such that it is possible to extract an eye region (in other words, a region including the iris) from the image V11 of the eyeball U11. Note that the eye region segmentation is disclosed in, for example, "N. Liu et al., "Accurate Iris Segmentation in Non-cooperative Environments Using Fully Convolutional Networks", IEEE ICB 2016".

The Purkinje image position detection unit 105 acquires the image V11 of the eyeball U11 captured by the image capturing unit 203 from the image capturing unit 203, and performs an image analysis with respect to the image V11, thereby detecting a position of a Purkinje image in the image V11. Note that Japanese Patent Application Laid-Open No. 2015-13031 or the like discloses a method relating to the extraction of the Purkinje image. Furthermore, although not illustrated in the example illustrated in FIG. 4, the input and output device 20 or the information processing device 10 may include a configuration required for the extraction of the Purkinje image, such as a light source for irradiating the eyeball U11 with infrared light, or a device which implements the configuration may be provided separately. Then, the Purkinje image position detection unit 105 outputs, to the gaze estimation unit 107, information indicating a result of detecting the position of the Purkinje image in the image V11 of the eyeball U11.

The pupil center estimation unit 103 acquires the image V11 of the eyeball U11 captured by the image capturing unit 203 from the image capturing unit 203. The pupil center estimation unit 103 extracts a partial image of a region including the iris in the acquired image V11 of the eyeball U11 and compares the partial image with the iris template stored in the storage unit 109 in advance, thereby estimating a position (also referred to as a "center position" of the pupil) of the center of the pupil in the image V11. Note that details of a processing relating to the estimation of the center position of the pupil will be described separately later. Then, the pupil center estimation unit 103 outputs, to the gaze estimation unit 107, information indicating a result of estimating the center position of the pupil in the image V11 of the eyeball U11.

The gaze estimation unit 107 acquires, from the Purkinje image position detection unit 105, the information indicating the result of detecting the position of the Purkinje image in the image V11 of the eyeball U11 captured by the image capturing unit 203. Furthermore, the gaze estimation unit 107 acquires, from the pupil center estimation unit 103, the information indicating the result of estimating the center position of the pupil in the image V11. Then, the gaze estimation unit 107 estimates a direction (in other words, a gaze direction) in which the gaze of the user is directed on the basis of the result of detecting the position of the Purkinje image and the result of estimating the center position of the pupil.

Then, the gaze estimation unit 107 outputs, to a predetermined output destination, information indicating a result of estimating the gaze direction. With such a configuration, for example, the information processing device 10 can use the result of estimating the gaze direction to perform various processing. Note that the pupil center estimation unit 103 and the gaze estimation unit 107 correspond to an example of an "estimation unit". Furthermore, in the pupil center estimation unit 103, a portion which acquires the image V11 from the image capturing unit 203 corresponds to an example of an "acquisition unit".

Note that the functional configuration of the information processing system 1 according to the present embodiment described above is merely an example, and as long as it is possible to implement the respective functions described above, the functional configuration of the information processing system 1 is not necessarily limited to the example illustrated in FIG. 4. As a specific example, some configurations of the information processing device 10 may be provided outside the information processing device 10. As a more specific example, some configurations (for example, the authentication processing unit 101) of the information processing device 10 may be provided in the input and output device 20. Furthermore, as another example, the respective functions of the information processing device 10 may be implemented by a plurality of devices cooperating with each other. Furthermore, as another example, the information processing device 10 and the input and output device 20 may be configured integrally to each other as described above. Furthermore, at least a part of the configuration corresponding to the information processing device 10 may be configured as an integrated circuit (for example, a semiconductor chip or the like) such as an IC or the like. In this case, for example, the integrated circuit may be embedded in the input and output device 20 (for example, an HMD, a smartphone, or the like).

Hereinabove, the example of the functional configuration of the information processing system according to the present embodiment has been described with reference to FIG. 4, focusing particularly on the configuration of the information processing device 10 described with reference to FIG. 1.

<3.2. Details of Processing Relating to Estimation of Central Position of Pupil>

Next, details of the processing relating to the estimation of the center position of the pupil will be described.

(Application of Rubber Sheet Model)

The information processing system according to the present embodiment compares information of the iris in the image V11 of the eyeball U11 captured by the image capturing unit 203 with information of the iris in the iris template (in other words, the image of the eyeball U11) acquired in advance, thereby estimating the center position of the pupil in the image V11. However, in general, since a diameter of the pupil changes depending on an environment such as illumination, or a state of the user, it can be presumed that it will be difficult to perform the comparison of the information of the iris between the image captured by the image capturing unit 203, and the iris template acquired in advance.

In this regard, a "rubber sheet model" is applied to the comparison of the iris information in the information processing system according to the present embodiment. The rubber sheet model is a model under the assumption that the iris pattern around the pupil dilates and contracts in a circumferential direction like a rubber in accordance with dilation and contraction of the pupil. For example, documents such as U.S. Pat. No. 5,291,560A and "How Iris Recognition Works, J. Daugman" disclose an example of a case of applying the rubber sheet model to the comparison of the iris pattern in the iris authentication.

Figure 8:
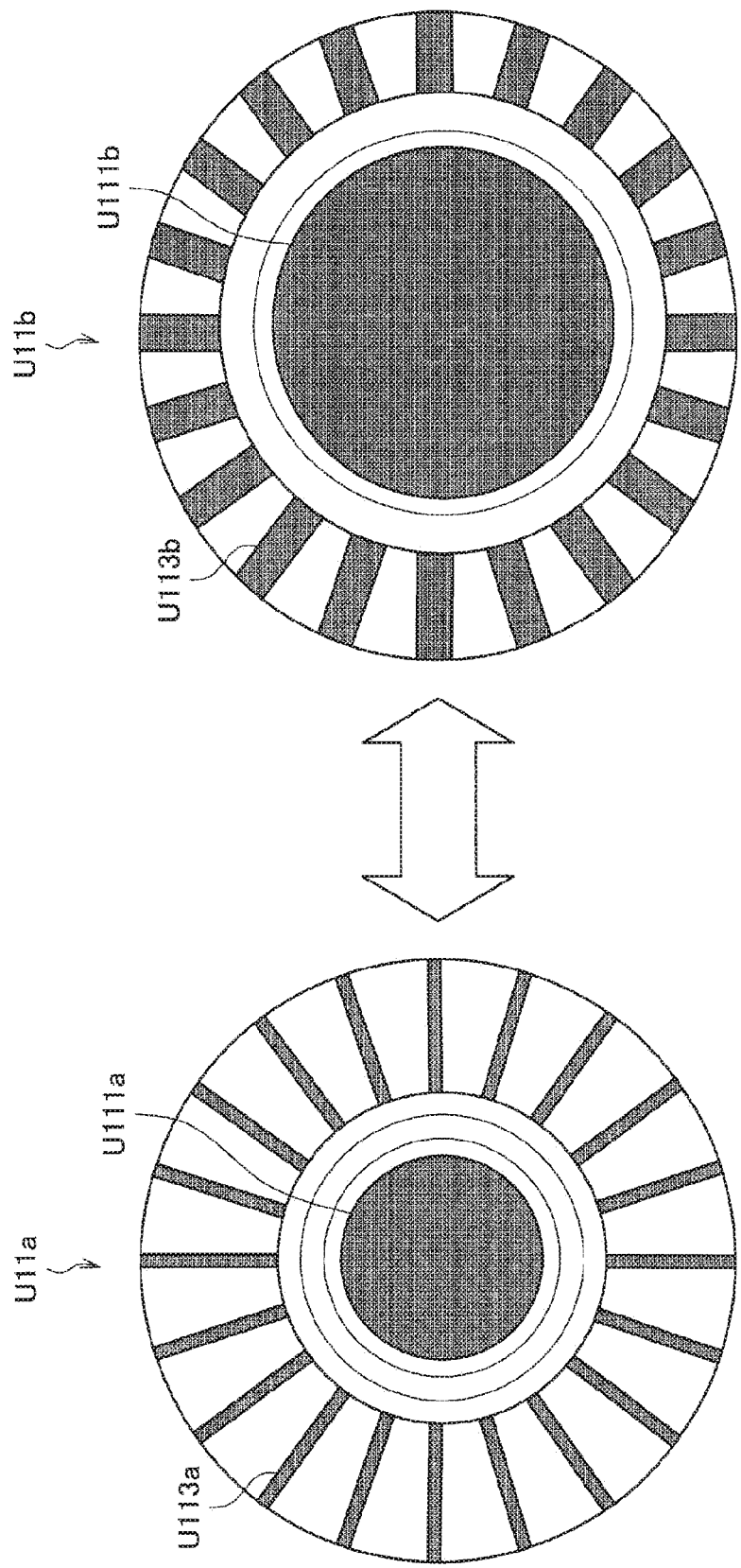
FIG. 8 is an explanatory view for describing an outline of a rubber sheet model.

For example, FIG. 8 is an explanatory view for describing an outline of the rubber sheet model. In FIG. 8, the left drawing schematically illustrates an eyeball U11a in a state in which a pupil contracts. In other words, Reference Sign U111a schematically indicates the pupil of the eyeball U11a. Furthermore, Reference Sign U113a schematically indicates an iris pattern of the eyeball U11a. Furthermore, the right drawing schematically illustrates an eyeball U11b in a state in which a pupil dilates. In other words, Reference Sign U111b schematically indicates the pupil of the eyeball U11b. Furthermore, Reference Sign U113b schematically indicates an iris pattern of the eyeball U11b.

(Flow of Processing Relating to Estimation of Central Position of Pupil)

Figure 9:
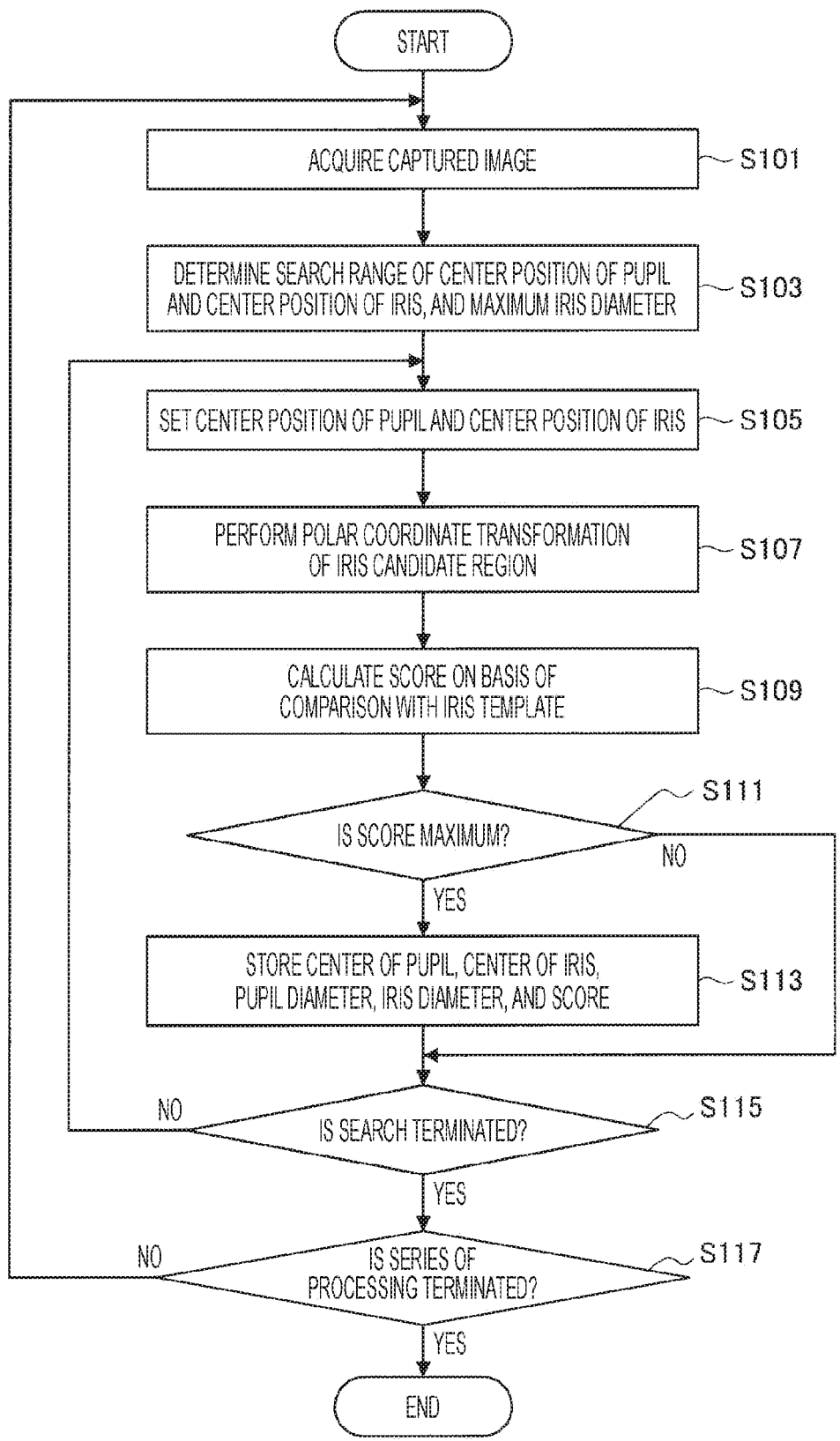
FIG. 9 is a flowchart illustrating an example of a flow of a series of processing in the information processing system according to the embodiment.

Next, an example of a flow of the processing relating to the estimation of the center position of the pupil in the image V11 of the eyeball U11 captured by the image capturing unit 203 will be described with reference to FIG. 9. FIG. 9 is a flowchart illustrating an example of a flow of a series of processing in the information processing system according to the embodiment, and particularly illustrates the flow of the processing relating to the estimation of the center position of the pupil.

As illustrated in FIG. 9, the information processing device (pupil center estimation unit 103) sequentially acquires the image V11 of the eyeball U11 captured by the image capturing unit 203, and the acquired image V11 becomes a target of the processing relating to the estimation of the center position of the pupil (S101).

Once the image V11 of the eyeball U11 is acquired, the information processing device 10 determines a search range of the center position of the pupil and a center position of the iris in the image V11, and a maximum iris diameter (S103). These parameters may be fixedly set in a case where, for example, a position and a size of an eye region (in other words, a region including the pupil and the iris) in the image V11 can be estimated in advance. Furthermore, as another example, an approximate position and an approximate size of the eye region may be determined on the basis of a method according to the related art, such as circular fitting or segmentation applied by the iris authentication or the like. Note that it is preferable that a method with a lower throughput is selected for determination of initial values of the parameters or the like according to performance of a processor for signal processing.

Next, the information processing device 10 sequentially sets points as respective candidates for the center position of the pupil and the center position of the iris in the set search range, and performs a processing relating to analysis and comparison as described later for each candidate, thereby specifying a candidate approximately matching the center position of the pupil among the candidates.

Specifically, the information processing device 10 sets points as respective candidates for the center position of the pupil and the center position of iris in the search range (S105). Note that in general, as the gaze is averted to the side, a difference in position between the center of the pupil and the center of the iris becomes large in a state in which the image capturing unit 203 and the eyeball U11 face each other. Therefore, in a case where the center of the pupil and the center of the iris are set individually, it is possible to perform detection of the eye region with a higher precision. However, in a case where a relative positional relationship between the image capturing unit 203 and the eyeball U11 can be estimated in advance, for example, only the center of the pupil becomes a search target, and a predetermined relative position according to the center position of the pupil may be specified as the center of the iris.

Figure 10:
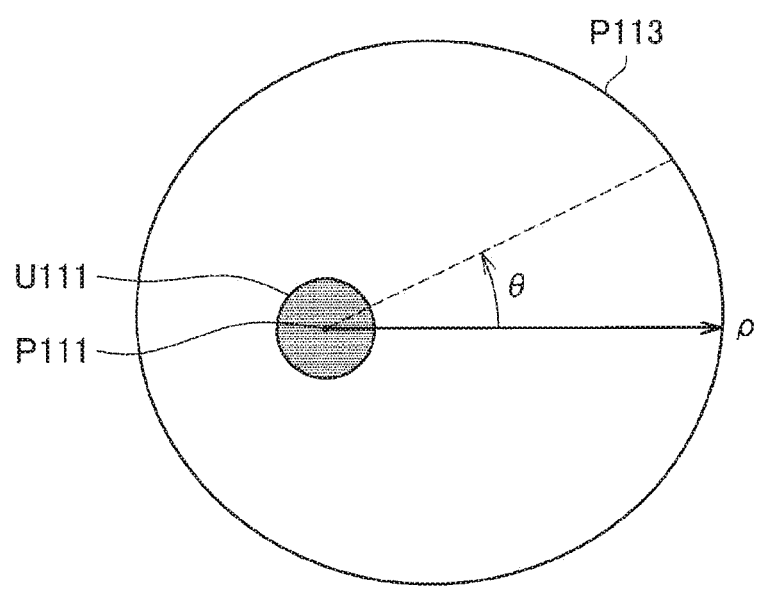
FIG. 10 is an explanatory view for describing an outline of a processing of performing a polar coordinate transformation of a region within a range of a maximum iris diameter.

Next, the information processing device 10 performs a polar coordinate transformation of a region within a range of the maximum iris diameter described above in the image V11 according to the setting of the points as the respective candidates for the center of the pupil and the center of the iris (S107). At this time, for example, it is preferable that the information processing device 10 performs the polar coordinate transformation while having a point set as the candidate for the center of the pupil as an origin along an iris circle. As a specific example, FIG. 10 is an explanatory view for describing an outline of a processing of a polar coordinate transformation of a region within a range of a maximum iris diameter. In FIG. 10, Reference Sign P111 schematically indicates a point set as the candidate for the center of the pupil U111. Furthermore, Reference Sign P113 schematically indicates the iris circle. Furthermore, ρ indicates a direction corresponding to radial coordinates in the polar coordinate transformation, and θ indicates a direction corresponding to angular coordinates in the polar coordinate transformation.

A positional relation between a pupil circle and the iris circle can change depending on a positional relation between the eyeball U11 and the image capturing unit 203, and a difference in gaze direction. Meanwhile, it is possible to obtain a polar coordinate image more rarely affected by the positional relation between the eyeball U11 and the image capturing unit 203, and the difference in gaze direction in the rubber sheet model through the polar coordinate transformation described above.

Figure 11:
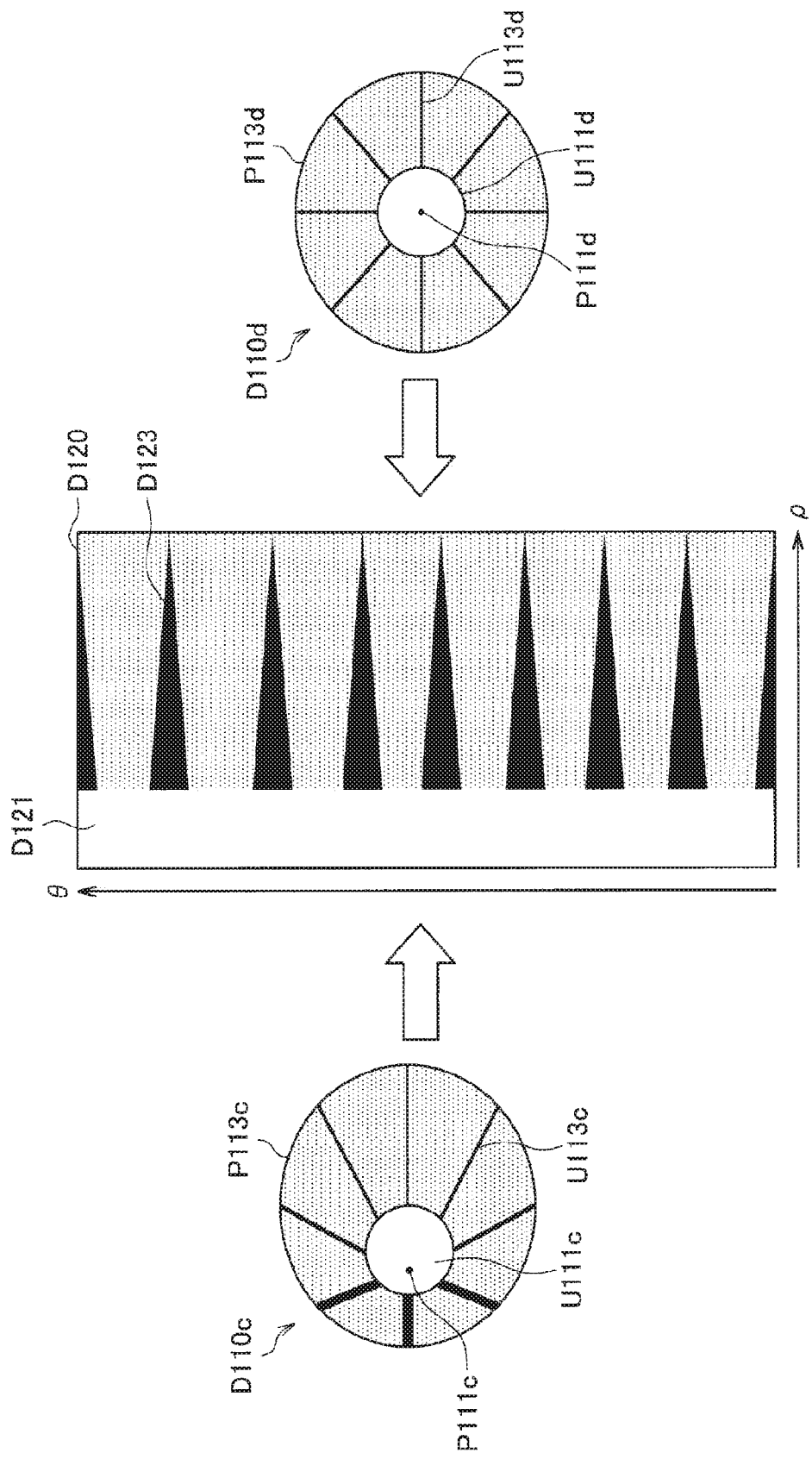
FIG. 11 is an explanatory view for describing an outline of a polar coordinate image obtained by performing the polar coordinate transformation of the region within the range of the maximum iris diameter.

For example, FIG. 11 is an explanatory view for describing an outline of a polar coordinate image obtained by the polar coordinate transformation of the region within the range of the maximum iris diameter. In FIG. 11, Reference Signs D110c and D110d schematically indicate partial images corresponding to regions in a range of the iris circle in the image V11 of the eyeball U11, respectively. Furthermore, Reference Sign D120 schematically illustrates a polar coordinate image obtained by performing the polar coordinate transformation of the partial images D110c and D110d, respectively.

Specifically, the partial image D110c corresponds to a partial image corresponding to a region in the range of the iris circle in a state in which the pupil is not directed to the image capturing unit 203 (or a state in which the pupil of the eyeball U11 and the image capturing unit 203 do not face each other). In other words, Reference Signs U111c and U113c schematically indicate regions of the pupil and the iris in the partial image D110c, respectively. Furthermore, Reference Sign P113c schematically indicates an iris circle in the partial image D110c. Furthermore, Reference Sign P111c schematically indicates the center of the pupil U111c. In other words, in the example illustrated in FIG. 11, it is possible to acquire the polar coordinate image D120 by performing the polar coordinate transformation of the partial image D110c of the iris circle P113c around the center P111c of the pupil as the center. Note that in the polar coordinate image D120, a region indicated by Reference Sign D121 corresponds to a region of the pupil. Furthermore, a region indicated by Reference Sign D123 corresponds to a region of the iris.

Furthermore, the partial image D110d corresponds to a partial image corresponding to a region in the range of the iris circle in a state in which the pupil is directed to the image capturing unit 203 (or a state in which the pupil of the eyeball U11 and the image capturing unit 203 face each other). In other words, Reference Signs U111d and U113d schematically indicate regions of the pupil and the iris in the partial image D110d, respectively. Furthermore, Reference Sign P113d schematically indicates an iris circle in the partial image D110c. Furthermore, Reference Sign P111d schematically indicates the center of the pupil U111d. In other words, in the example illustrated in FIG. 11, it is possible to acquire the polar coordinate image D120 by performing the polar coordinate transformation of the partial image D110d of the iris circle P113d around the point P111d as the center.

In other words, in a case where it is presumed that the rubber sheet model is applied, ideally, it is possible to acquire the similar polar coordinate image D120 even in a situation in which the positional relation between the eyeball U11 and the image capturing unit 203 and the gaze directions are different from each other like the partial images D110c and D110d in FIG. 11. Furthermore, through the polar coordinate transformation, it is possible to convert a partial image (for example, the partial images D110c and D110d) having a substantially circular shape and corresponding to the region of the iris circle into a polar coordinate image (for example, the polar coordinate image D120) having a substantially rectangular shape. With this arrangement, for example, an increase in access speed by line access is expected in comparison to a case of analyzing the partial image having a substantially circular shape and corresponding to the region of the iris circle. Furthermore, since parallel processing is possible, an improvement in speed performance of the overall processing is also expected. Note that it is preferable that the iris template acquired at the time of the iris authentication is also converted into a polar coordinate image through the polar coordinate transformation, similarly. Note that for convenience, the polar coordinate image including the region of the iris based on an image capturing result (in other words, the captured image V11 of the eyeball U11) obtained by the image capturing unit 203 will also be referred to as a "polar coordinate image Rc" in the following description. Furthermore, the polar coordinate image corresponding to the iris template acquired in advance at the time of the iris authentication will also be referred to as a "polar coordinate image Rt". Note that the polar coordinate image Rc corresponds to an example of a "first polar coordinate image". Furthermore, the polar coordinate image Rt corresponds to an example of a "second polar coordinate image".

Next, as illustrated in FIG. 9, the information processing device 10 compares the polar coordinate image Rc based on the image capturing result obtained by the image capturing unit 203 with the polar coordinate image Rt corresponding to the iris template to calculate a score (matching score) indicating a degree of matching between the polar coordinate images (S109). Here, the conversion into the polar coordinate image having the substantially rectangular shape is performed through the polar coordinate transformation described above, such that a general method for image matching such as block matching or normalized correlation can be used to calculate the score in the comparison between the images.

Note that at the time of performing the comparison between the images, the polar coordinate image Rc based on the image capturing result obtained by the image capturing unit 203, and the polar coordinate image Rt corresponding to the iris template are adjusted (for example, scaled) so that heights thereof corresponding to a θ direction substantially coincide with each other, such that it is possible to simplify a processing relating to the comparison. Hereinafter, a description will be provided under the assumption that the polar coordinate image Rc based on the image capturing result obtained by the image capturing unit 203, and the polar coordinate image corresponding to the iris template are adjusted so that the heights corresponding to the θ direction substantially coincide with each other.

Furthermore, as for the image acquired as the iris template in advance, it is preferable that an image obtained by extracting only a region corresponding to the iris in advance is applied on the basis of a method according to the related art, such as circular fitting or segmentation. With this arrangement, for example, it is possible to easily implement the processing using the iris template with a high precision, and it is possible to reduce a size of the storage region in which the iris template is retained.

Here, the processing relating to the comparison between the polar coordinate image Rc based on the image capturing result obtained by the image capturing unit 203, and the polar coordinate image Rt corresponding to the iris template will described in more detail with reference to FIGS. 12A and 12B. FIGS. 12A and 12B are explanatory views for describing a processing relating to a comparison between polar coordinate images by the information processing device according to the embodiment. In FIGS. 12A and 12B, the left drawing schematically illustrates the polar coordinate image Rt acquired as the iris template in advance. Furthermore, the right drawing schematically illustrates the polar coordinate image Rc based on the image capturing result obtained by the image capturing unit 203. Note that in the example illustrated in FIGS. 12A and 12B, only the region corresponding to the iris is cut out as the polar coordinate image Rt corresponding to the iris template. Furthermore, it is preferable that the entire iris pattern is included in the polar coordinate image Rc. Therefore, it is more preferable that the maximum iris diameter is set to be large at the time of generating the polar coordinate image Rc. Note that a region (in other words, a region corresponding to an inner portion of the iris circle) corresponding to the polar coordinate image Rc will also be referred to as an "iris candidate region" for convenience in the following description.

As illustrated in FIGS. 12A and 12B, the iris candidate region corresponding to the polar coordinate image Rc based on the image capturing result obtained by the image capturing unit 203 includes a region (hereinafter, also referred to as a "pupil region") corresponding to the pupil and a region (hereinafter, also referred to as an "outside-iris region") corresponding to the outside of the iris, such as an eyelid, the white of the eye, and the like in some cases. Furthermore, in a case where the eyeball rotates in a roll direction, a phase of the iris pattern included in the iris candidate region (in other words, the polar coordinate image Rc) is misaligned with respect to the iris template (that is, the polar coordinate image Rt) in the θ direction (a vertical direction in FIGS. 12A and 12B) in some cases. In consideration of such a situation, at the time of the comparison between the polar coordinate image Rc and the polar coordinate image Rt, it is preferable that conditions of various parameters are sequentially adjusted in the polar coordinate image Rc to search for a condition having a higher score.

Figure 13:
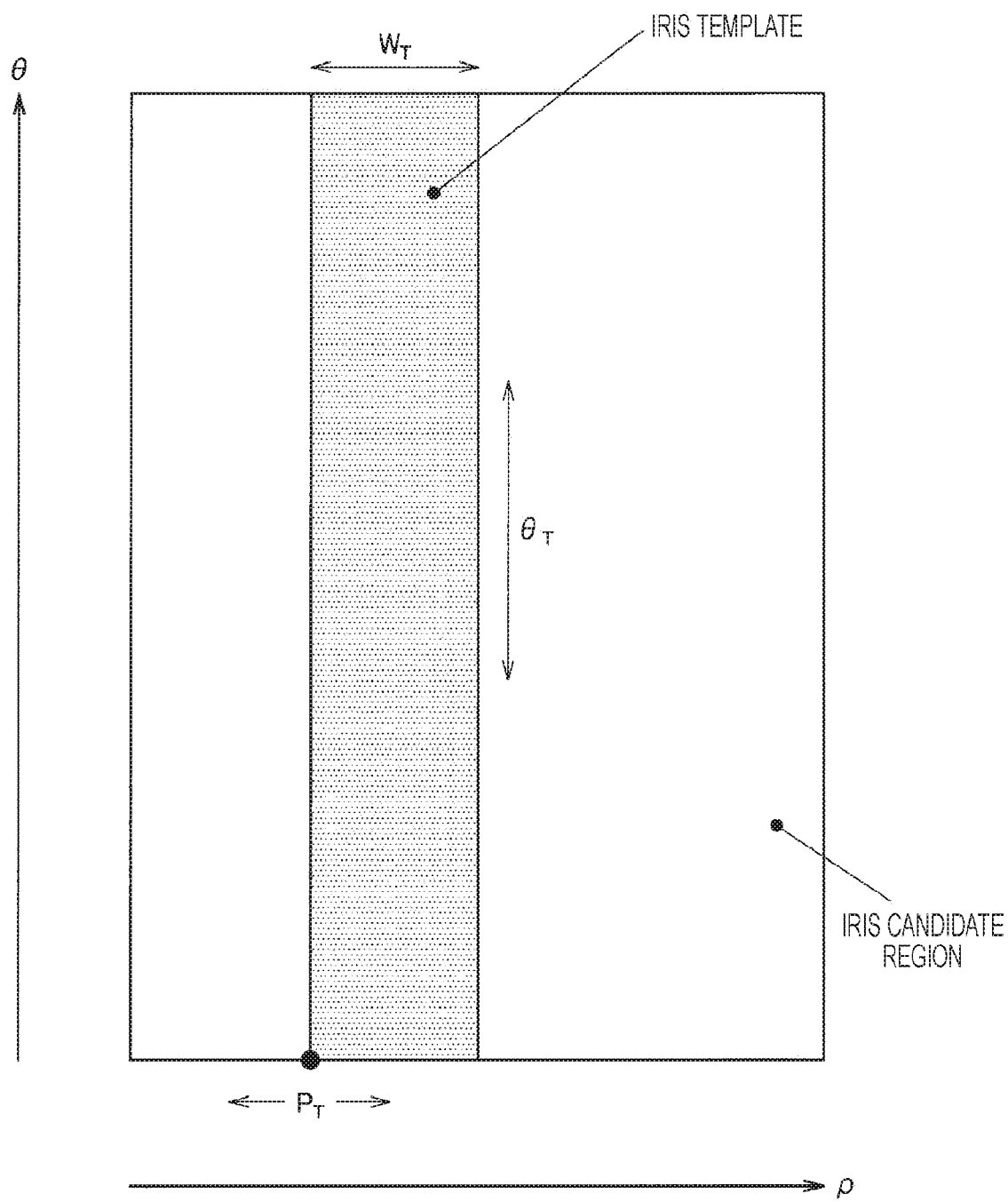
FIG. 13 is an explanatory view for describing a processing relating to a comparison between polar coordinate images by the information processing device according to the embodiment.

For example, FIG. 13 is an explanatory view for describing the processing relating to the comparison between the polar coordinate images by the information processing device according to the present embodiment, and illustrates an example of parameters of the polar coordinate image Rc as an adjustment target. In FIG. 13, a parameter $P_T$ indicates a start position of a region (in other words, a region corresponding to the iris template) corresponding to the iris in a ρ direction in the iris candidate region. Furthermore, $W_T$ indicates a width of the region corresponding to the iris in the ρ direction in the iris candidate region. Furthermore, $θ_T$ indicates a phase of the iris pattern included in the iris candidate region in the θ direction.

In other words, it is preferable that the information processing device 10 searches for the condition having the higher score between the polar coordinate image Rc and the polar coordinate image Rt while sequentially changing a condition of each of the start position $P_T$ of the region corresponding to the iris, the width $W_T$ of the region, and the phase $θ_T$ of the iris pattern in the polar coordinate image Rc.

In this way, the information processing device 10 searches for a condition of a parameter having a higher score in the polar coordinate image Rc having a point set as a candidate for the center of the pupil as an origin, and the condition which is searched for is set as a parameter of the polar coordinate image Rc corresponding to the candidate for the center of the pupil. In other words, the information processing device 10 calculates the score while sequentially changing the conditions (in other words, the parameters $P_T$, $W_T$, and $θ_T$) to search for the condition under which the score becomes highest. Then, as illustrated in FIG. 9, in a case where the score corresponding to the condition is higher than a score calculated in the past (in other words, in a case where the score is highest) (S111, YES), the information processing device 10 stores information including the center position of the pupil, the center position of the iris, the pupil diameter, and the iris diameter at this time together with the score (S113). Note that in a case where the score corresponding to the condition is lower than the score calculated in the past (in other words, in a case where the score is not highest) (S111, NO), the information may not be stored.

In this way, the information processing device 10 sequentially performs a series of processing indicated by Reference Signs S107 to S113 for each point as the candidate for each of the center position of the pupil and the center position of the iris in the search range (S115, NO), while sequentially changing the point as the candidate (S105). Then, the information processing device 10 performs the processing with respect to all points as the candidate for each of the center position of the pupil and the center position of the iris in the search range, and finally outputs, as a final result, information regarding a point which has the highest score as the candidate for each of the center position of the pupil and the center position of the iris. In other words, the information output as the final result indicates an actual position and size of each of the pupil and the iris.

Then, once the search in the search range is terminated (S115, YES), the information processing device 10 acquires an image V11 of the eyeball U11 newly captured by the image capturing unit 203 as a new target (S101). In this way, unless the termination of the series of processing is instructed (S117, NO), the information processing device 10 performs the series of processing indicated by Reference Signs S101 to S115. Then, once the termination of the series of processing is instructed (S117, YES), the information processing device 10 terminates performing the series of processing indicated by Reference Signs S101 to S117.

Hereinabove, the example of the flow of the processing relating to the estimation of the center position of the pupil in the image V11 of the eyeball U11 captured by the image capturing unit 203 has been described with reference to FIGS. 9, 10, 11, 12A, 12B, and 13.

<3.3. Modified Example>

Next, another example of the processing relating to the estimation of the center position of the pupil in the image of the eyeball will be described as a modified example of the information processing system according to the present embodiment.

In the example described as the embodiment, the comparison between the polar coordinate image Rc (in other words, the polar coordinate image based on the image capturing result obtained by the image capturing unit 203) of the iris candidate region, and the polar coordinate image Rt corresponding to the iris template is performed for each point as the candidate for each of the center position of the pupil and the center position of the iris. In other words, as the comparison between the images is performed, a throughput tends to become relatively large. Although it is possible to increase a processing speed by parallelizing the comparison between the images, in the present modified example, an example of a method of increasing the processing speed by further simplifying the processing relating to the comparison will be described.

Figure 14:
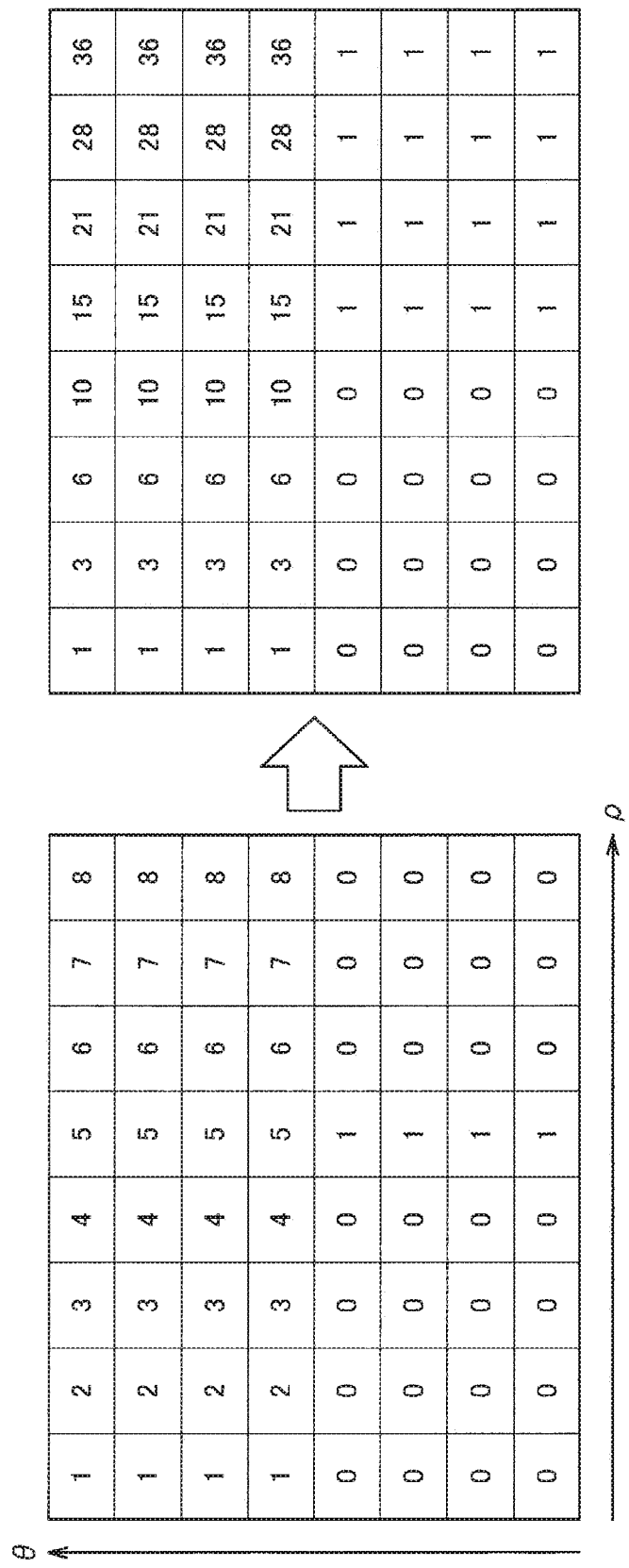
FIGS. 14A and 14B are explanatory views for describing an outline of an information processing system according to a modified example.

For example, FIGS. 14A and 14B are explanatory views for describing an outline of an information processing system according to a modified example. In FIGS. 14A and 14B, the left drawing schematically illustrates each pixel of the polar coordinate image described above, and a pixel value (for example, a brightness value) of the pixel. In other words, the left drawing in FIGS. 14A and 14B illustrates a polar coordinate image of 8×8 pixels, and each value indicates a pixel value of a corresponding pixel.

The information processing device 10 according to the modified example converts the polar coordinate image Rc of the iris candidate region into an integral image obtained by sequentially integrating a pixel value of each pixel in a direction (in other words, the ρ direction) corresponding to the radial coordinates in the polar coordinate transformation. For example, the right drawing in FIGS. 14A and 14B illustrates an example of the integral image converted from the polar coordinate image illustrated as the left drawing.

Specifically, the information processing device 10 sequentially integrates the pixel values (in other words, averages the pixel values for each row) while projecting each pixel of the polar coordinate image in the ρ direction to convert the polar coordinate image into the integral image. Note that it is preferable that the polar coordinate image Rt corresponding to the iris template is also converted into an integral image through a similar method. According to such a control, for example, it is also possible to dimensionally compress a polar coordinate image Rt of $M_\rho$ rows and $N_\theta$ columns, which corresponds to the iris template, to an image of $M_\rho$ rows and one column. Note that the integral image converted from the polar coordinate image Rc corresponds to an example of a "first integral image". Furthermore, the integral image converted from the polar coordinate image Rt corresponds to an example of a "second integral image".

Here, in a case where it is assumed that the iris pattern has a substantially radial shape to which the rubber sheet model can be applied, it is possible to more simply calculate the score by performing comparison of one-dimensional data after projection between the polar coordinate image Rt and the polar coordinate image Rc, in comparison to the comparison between the images.

As a specific example, a case where a fifth column to a seventh column are extracted as the region corresponding to the iris from the polar coordinate image of 8×8 pixels illustrated as the left drawing in FIGS. 14A and 14B will be described. In this case, a vector (for example, a vector obtained by division by a width (=3) in the ρdirection) obtained by normalizing, by the width (=3) in the ρ direction, a difference vector obtained by subtracting a θ direction one-dimensional vector of a fourth column from a θ direction one-dimensional vector of the seventh column in the integral image illustrated in the right drawing, becomes a projection value (in other words, a θ direction one-dimensional vector) corresponding to the region as an extraction target. In this way, the projection vector of the region as the target may be calculated from the polar coordinate image Rc, and a sum of absolute difference (SAD), normalized correlation, and the like between the projection vector and a projection vector calculated on the basis of the polar coordinate image Rt may be calculated to perform a comparison between the projection vectors. With this arrangement, it is possible to calculate costs with less calculations in comparison to a case of comparing between the images according to the related art. Particularly, the comparison between the images according to the related art needs to be performed while performing scaling of the image in some cases. Whereas, according to the present method, a range in which the difference vector is calculated is appropriately changed, such that a processing relating to scaling of the integral image need not be performed. Therefore, it is possible to reduce the calculations in comparison to the comparison between the images according to the related art.

Furthermore, the information processing device 10 may perform the comparison of the projection vectors between the polar coordinate image Rc and the polar coordinate image Rt while sequentially changing conditions of the start position $P_T$ of the region corresponding to the iris, and the width $W_T$ of the region in, for example, the integral image converted from the polar coordinate image Rc. According to such a control, it is possible to specify the region corresponding to the iris on the basis of the condition having a higher cost calculated, even in a situation in which, for example, the region corresponding to the iris in the polar coordinate image Rc is not specified.

Furthermore, according to a known technology, it is also possible to exclude a region such as an eyelid, which can be present in the iris circle, as an ineffective region through a mask processing in advance. Furthermore, it is possible to specify a mask region in the iris circle through, for example, a known segmentation processing. Therefore, for example, when calculating the projection vector described above in the information processing system according to the modified example, it is also possible to calculate the score with a higher precision by performing the calculating after excluding the mask region (in other words, the region such as the eyelid).

Hereinabove, another example of the processing relating to the estimation of the center position of the pupil in the image of the eyeball has been described as the modified example of the information processing system according to the present embodiment with reference to FIGS. 14A and 14B.

<<4. Example of Hardware Configuration>>

Figure 15:
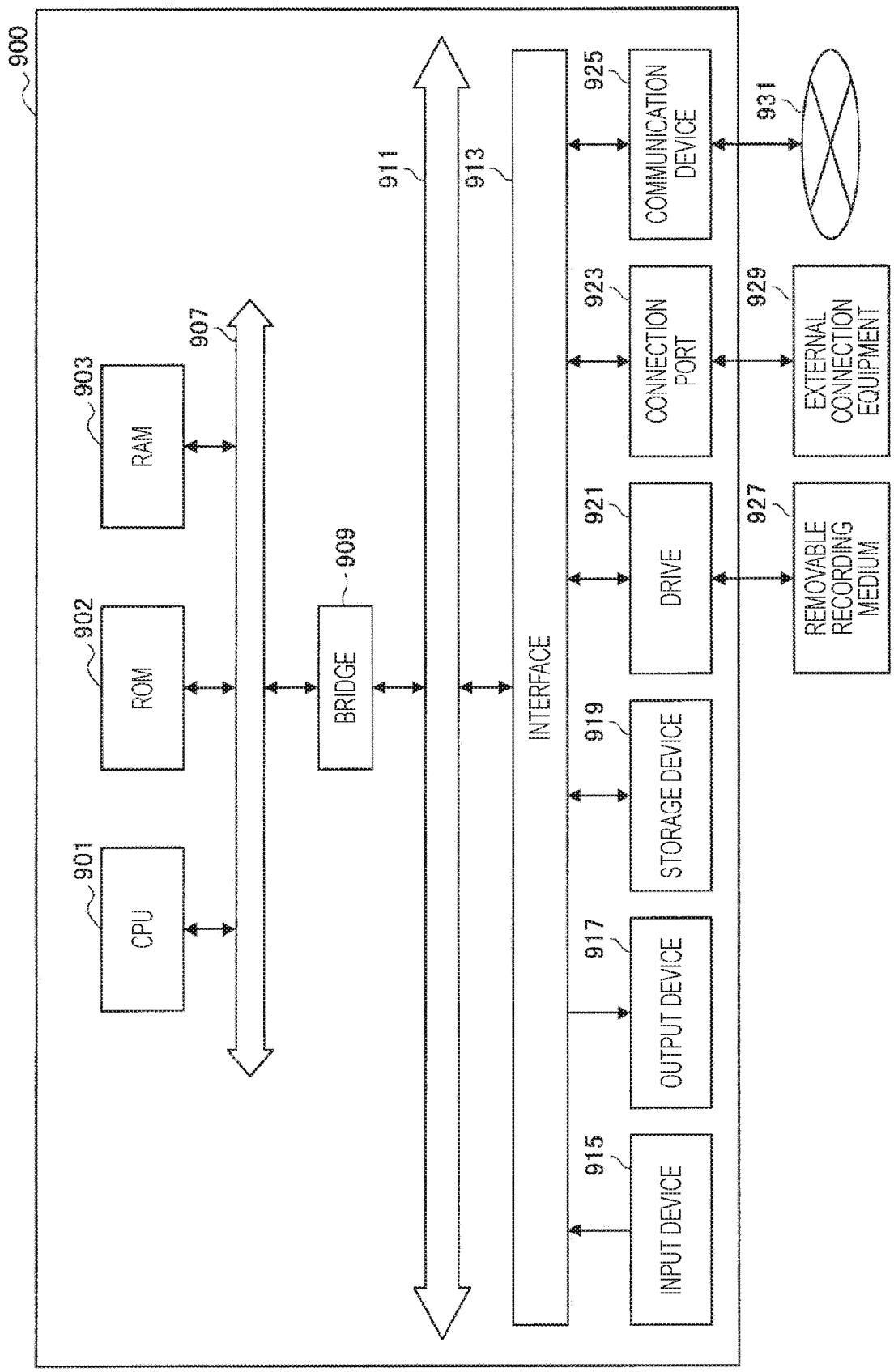

Next, an example of a hardware configuration of an information processing device constituting an information processing system according to an embodiment of the present disclosure, like the information processing device 10 and the input and output device 20 described above, will be described in detail with reference to FIG. 15. FIG. 15 is a functional block diagram illustrating a configuration example of a hardware configuration of an information processing device constituting a communication system according to an embodiment of the present disclosure.

An information processing device 900 constituting the communication system according to the present embodiment mainly includes a central processing unit (CPU) 901, a read-only memory (ROM) 902, and a random access memory (RAM) 903. Furthermore, the information processing device 900 further includes a host bus 907, a bridge 909, an external bus 911, an interface 913, an input device 915, an output device 917, a storage device 919, a drive 921, a connection port 923, and a communication device 925.

The CPU 901 functions as an operation processing device and a control device, and controls a part or all of the operations in the information processing device 900 according to various programs recorded in the ROM 902, the RAM 903, the storage device 919, or a removable recording medium 927. The ROM 902 stores a program, an operation parameter, and the like used by the CPU 901. The RAM 903 primarily stores the program used by the CPU 901, and a parameter or the like which appropriately changes in executing the program. These are connected to one another through the host bus 907 implemented by an internal bus such as a CPU bus. For example, the authentication processing unit 101, the pupil center estimation unit 103, the Purkinje image position detection unit 105, and the gaze estimation unit 107 illustrated in FIG. 4 can be implemented by the CPU 901.

The host bus 907 is connected to the external bus 911 such as a peripheral component interconnect/interface (PCI) through the bridge 909. Furthermore, the input device 915, the output device 917, the storage device 919, the drive 921, the connection port 923, and the communication device 925 are connected to the external bus 911 through the interface 913.

The input device 915 is, for example, operation means such as a mouse, a keyboard, a touch panel, a button, a switch, a lever, a pedal, or the like operated by the user. Furthermore, the input device 915 may be, for example, motor control means (so-called remote controller) using infrared light or another electric wave, or may be external connection equipment 929 such as a mobile phone, a personal digital assistant (PDA), or the like corresponding to the operation of the information processing device 900. Moreover, the input device 915 is implemented by an input control circuit which generates an input signal on the basis of, for example, information input from the user by using the operation means, and outputs the input signal to the CPU 901, or the like. The user of the information processing device 900 operates the input device 915 to input various data to the information processing device 900 or instruct the information processing device 900 to perform a processing operation.

The output device 917 is implemented by a device which can visually or acoustically notify the user of the acquired information. Such a device includes a display device such as a cathode-ray tube (CRT) display device, a liquid crystal display device, a plasma display device, an electroluminescent (EL) display device, or a lamp, a voice output device such as a speaker or a headphone, a printer device, and the like. The output device 917 outputs, for example, a result obtained by various processing performed by the information processing device 900. Specifically, the display device displays the result obtained by various processing performed by the information processing device 900 as a text or an image. On the other hand, the voice output device converts an audio signal including data of reproduced voice, sound, or the like into an analog signal, and outputs the analog signal.

The storage device 919 is a device for storing data, the device being configured as an example of a storage unit of the information processing device 900. The storage device 919 may be implemented by, for example, a magnetic storage device such as a hard disk drive (HDD), a semiconductor storage device, an optical storage device, a magneto-optical storage device, or the like. The storage device 919 stores a program executed by the CPU 901, various data, or the like. For example, the storage unit 109 illustrated in FIG. 4 can be implemented by the storage device 919.

The drive 921 is a reader/writer for a recording medium and is embedded in or externally attached to the information processing device 900. The drive 921 reads information recorded in the mounted removable recording medium 927 such as a magnetic disk, an optical disk, a magneto-optical disk, or a semiconductor memory, and outputs the read information to the RAM 903. Furthermore, the drive 921 can also write a record in the mounted removable recording medium 927 such as a magnetic disk, an optical disk, a magneto-optical disk, a semiconductor memory, or the like. The removable recording medium 927 is, for example, digital versatile disc (DVD) media, high-definition (HD)-DVD media, Blu-ray (registered trademark) media, or the like. Furthermore, the removable recording medium 927 may also be CompactFlash (CF) (registered trademark), a flash memory, a secure digital (SD) memory card, or the like. Furthermore, the removable recording medium 927 may also be, for example, an integrated circuit (IC) card, electronic equipment, or the like in which a non-contact type IC chip is mounted.

The connection port 923 is a port for direct connection to the information processing device 900. As an example, the connection port 923 is a universal serial bus (USB) port, an IEEE 1394 port, a small computer system interface (SCSI) port, or the like. As another example, the connection port 923 is a recommended standard 232C (RS-232C) port, an optical audio terminal, a high-definition multimedia interface (HDMI) (registered trademark), or the like. As the external connection equipment 929 is connected to the connection port 923, the information processing device 900 directly acquires various data from the external connection equipment 929 or provides various data to the external connection equipment 929.

The communication device 925 is, for example, a communication interface implemented by a communication device or the like for connection to a communication network (network) 931. The communication device 925 is, for example, a communication card or the like for a wired or wireless local area network (LAN), Bluetooth (registered trademark), or wireless USB (WUSB). Furthermore, the communication device 925 may also be a router for optical communication, a router for asymmetric digital subscriber line (ADSL), a modem for various communication, or the like. The communication device 925 can, for example, transmit and receive a signal or the like according to a predetermined protocol such as a transmission control protocol/Internet protocol (TCP/IP) or the like, to and from the Internet or another communication equipment. Furthermore, the communication network 931 connected to the communication device 925 is implemented by a network or the like connected in a wired or wireless manner, and may be, for example, the Internet, a home LAN, infrared communication, radio wave communication, satellite communication, or the like.

Hereinabove, the example of the hardware configuration which can implement the functions of the information processing device 900 constituting the communication system according to the embodiment of the present disclosure. The respective constituent elements described above may be implemented by using a commonly used member, or may be implemented by hardware specialized in the functions of the respective constituent elements. Accordingly, it is possible to appropriately change the used hardware configuration according to a technical level at each time when the present embodiment is implemented. Note that although not illustrated in FIG. 15, it goes without saying that various configurations corresponding to the information processing device 900 constituting the information processing system are included.

Note that it is possible to produce a computer program for implementing the respective functions of the information processing device 900 constituting the information processing system according to the present embodiment described above and install the computer program in a personal computer or the like. Furthermore, it is possible to provide a computer-readable recording medium in which such a computer program is stored. The recording medium is, for example, a magnetic disk, an optical disk, a magneto-optical disk, a flash memory, or the like. Furthermore, the computer program may be distributed through, for example, a network without using the recording medium. Furthermore, the number of computers executing the computer program is not particularly limited. For example, the computer program may also be executed by a plurality of computers (for example, a plurality of servers or the like) cooperating with each other.

<<5. Conclusion>>

As described above, in the information processing system 1 according to the present embodiment, the information processing device 10 acquires information regarding an iris in an eyeball and estimates a center position of a pupil in the eyeball on the basis of the information regarding the iris. Specifically, the information processing device 10 extracts a partial image of a region including the iris from an image of the eyeball captured by the predetermined image capturing unit 203, and estimates the center position of the pupil on the basis of the extracted partial image. As a more specific example, the information processing device 10 performs a polar coordinate transformation of the partial image of the region including the iris, around a point in a region corresponding to the pupil as the center to generate a polar coordinate image, the partial image being extracted from the image of the eyeball captured by the image capturing unit 203. Furthermore, the information processing device 10 compares the generated polar coordinate image with a polar coordinate image corresponding to a previously generated iris template. The information processing device 10 performs the comparison between the polar coordinate images for each point in the region (in other words, a search region) corresponding to the pupil, and estimates that a point corresponding to a polar coordinate image having a smaller difference from the iris template approximately matches the center position of the pupil.

With the configuration described above, by the information processing system according to the present embodiment, it is possible to detect the center position of the pupil with a higher precision in comparison to the method according to the related art, even in a situation in which it is difficult to acquire an image of the entire pupil covered by an eyelid or the like. In other words, by the information processing system according to the present embodiment, it is possible to further improve a precision in detecting a gaze of a user.

Furthermore, as described above with reference to FIG. 11, in the information processing system according to the present embodiment, the rubber sheet model is applied and the center position of the pupil may be estimated on the basis of the polar coordinate image obtained by performing the polar coordinate transformation of the partial image including the pupil and the iris. With such a configuration, it is possible to detect the center position (even the gaze of the user) of the pupil with a high precision even in a situation in which a positional relation between the eyeball and the image capturing unit 203, or a gaze direction changes. Note that the configuration relating to the estimation of the center position of the pupil based on the polar coordinate image obtained by performing the polar coordinate transformation of the partial image including the pupil and the iris is merely an example, and the configuration of the information processing system according to the present embodiment is not necessarily limited thereto. In other words, as long as it is possible to estimate the center position of the pupil on the basis of the partial image of the region including the iris in the image of the eyeball, the configuration of the information processing system, and the method relating to the estimation are not particularly limited.

Furthermore, in the example described above, the example in which the image acquired at the time of iris authentication and including the pupil and the iris is used as the iris template has been described. However, as long as it is possible to acquire the iris template before the processing relating to the estimation of the center of the pupil, a method or a timing for acquiring the iris template is not particularly limited. As a specific example, a trigger relating to registration of the iris template may be explicitly provided. Furthermore, as another example, the iris template may be dynamically acquired. As a specific example, the iris template may be generated on the basis of a more suitable image (for example, an image in which images of a wider range of the pupil and the iris are captured) among images sequentially captured by the image capturing unit 203.

Furthermore, as described above, in the information processing system according to the present embodiment, the image of the eyeball acquired as the iris template in advance may not necessarily include the entire iris. Note that in a case where the iris template is generated on the basis of the image in which the captured range of the iris is wider, a precision in estimating the center position of the pupil is improved as described above.

Note that the example in which the image of the eyeball captured by the predetermined image capturing unit and including the iris is used as the information regarding the iris has been described above, but as long as it is possible to implement the processing relating to the estimation of the center position of the pupil described above, an aspect of the information is not particularly limited. As a specific example, information (for example, a feature amount of the iris portion, or the like) obtained as a result of performing image analysis with respect to the image of the eyeball including the iris may be acquired as the information regarding the iris. In this case, for example, the information processing device 10 may reconfigure the iris template and information (for example, the polar coordinate image) of an iris candidate region compared with the iris template, on the basis of the acquired information. Furthermore, as another example, the partial image extracted from the image of the eyeball and including the pupil and the iris, and the polar coordinate image obtained by performing the polar coordinate transformation of the partial image may be acquired as the information regarding the iris. Note that in this case, the processing relating to the extraction of the partial image and the processing relating to the polar coordinate transformation may not be performed again.

Furthermore, although the processing in a case of detecting the gaze of the user has been mainly described above, the processing of estimating the center position of the pupil in the information processing system according to the present embodiment is not necessarily applied only to the gaze detection. In other words, in a case of a system requiring a processing relating to the estimation or detection of the center position of the pupil, the technology according to the present disclosure can be applied to the processing. Furthermore, it goes without saying that the configuration and the aspect of the device (for example, the input and output device 20 or the like) constituting the system can be appropriately changed depending on where the technology according to the present disclosure is applied.

Hereinabove, the preferred embodiment of the present disclosure has been described in detail with reference to the accompanying drawings, but the technical scope of the present disclosure is not limited to such examples. It is obvious that those having ordinary knowledge in the technical field of the present disclosure can conceive of various modifications or alterations within the scope of the technical idea described in the claims, and it is understood that the modifications or alterations naturally fall within the technical scope of the present disclosure.

Furthermore, the effects described in the present specification are merely illustrative or exemplary, and not limiting. That is, the technology according to the present disclosure may achieve other effects apparent to those skilled in the art from the description of the present specification, in addition to or instead of the effects described above.

Note that the following configurations also fall within the technical scope of the present disclosure.

(1)

An information processing device including:

an acquisition unit that acquires information regarding an iris in an eyeball; and an estimation unit that estimates a center position of a pupil in the eyeball on the basis of the information regarding the iris.

(2)

The information processing device according to (1), in which the acquisition unit acquires an image of the eyeball as the information regarding the iris, the image being captured by a predetermined image capturing unit, and the estimation unit extracts, from the image, a partial image of a region including the iris, and estimates the center position of the pupil on the basis of the extracted partial image.

(3)

The information processing device according to (2), in which the estimation unit performs a polar coordinate transformation of the partial image around a point in a region corresponding to the pupil as the center to generate a polar coordinate image, and estimates the center position of the pupil on the basis of the polar coordinate image.

(4)

The information processing device according to (3), in which the estimation unit estimates the center position of the pupil on the basis of a comparison between a first polar coordinate image and a second polar coordinate image, the first polar coordinate image being the generated polar coordinate image and the second polar coordinate image being another previously generated polar coordinate image.

(5)

The information processing device according to (4), in which the estimation unit estimates the center position of the pupil on the basis of a comparison between a region of the iris in the first polar coordinate image, and a region of the iris in the second polar coordinate image.

(6)

The information processing device according to (5), in which the estimation unit sequentially changes conditions relating to an area of a region extracted as the region of the iris from the first polar coordinate image, and estimates the center position of the pupil on the basis of a comparison between the region of the iris in the first polar coordinate image corresponding to each condition of the area, and the region of the iris in the second polar coordinate image.

(7)

The information processing device according to (5) or (6), in which the estimation unit sequentially controls a phase of the region of the iris in the first polar coordinate image in a direction corresponding to angular coordinates in the polar coordinate transformation, and estimates the center position of the pupil on the basis of a comparison between the region of the iris in the first polar coordinate image, of which the phase is controlled, and the region of the iris in the second polar coordinate image.

(8)

The information processing device according to any one of (4) to (7), in which the estimation unit generates the first polar coordinate image for each of a plurality of points in the region corresponding to the pupil, and estimates the center position of the pupil on the basis of a comparison between the first polar coordinate image corresponding to each of the plurality of points, and the second polar coordinate image.

(9)

The information processing device according to (8), in which the estimation unit estimates that a point corresponding to the first polar coordinate image having a smaller difference from the second polar coordinate image among the plurality of points approximately matches the center position of the pupil.

(10)

The information processing device according to (3), in which the estimation unit integrates each pixel value of the polar coordinate image in a direction corresponding to radial coordinates in the polar coordinate transformation to generate an integral image, and estimates the center position of the pupil on the basis of the integral image.

(11)

The information processing device according to (10), in which the estimation unit estimates the center position of the pupil on the basis of a comparison between a first integral image and a second integral image, the first integral image being the generated integral image and the second integral image being another previously generated integral image.

(12)

The information processing device according to (11), in which the estimation unit estimates the center position of the pupil on the basis of an integral value of the pixel value in the region of the iris in the first integral image, and an integral value of the pixel value in the region of the iris in the second integral image.

(13)

The information processing device according to (12), in which the estimation unit estimates the center position of the pupil on the basis of a comparison between a value obtained by normalizing the integral value of the pixel value in the region of the iris in the first integral image according to a width of the region of the iris, and a value obtained by normalizing the integral value of the pixel value in the region of the iris in the second integral image according to a width of the region of the iris.

(14)

The information processing device according to any one of (3) to (13), in which the region has a substantially circular shape, and the polar coordinate image has a substantially rectangular shape.

(15)

The information processing device according to any one of (1) to (14), in which the estimation unit estimates a direction of a gaze on the basis of a result of estimating the center position of the pupil.

(16)

An information processing method including:

acquiring, by a computer, information regarding an iris in an eyeball; and estimating, by the computer, a center position of a pupil in the eyeball on the basis of the information regarding the iris.

(17)

A program causing a computer to execute:

acquiring information regarding an iris in an eyeball; and estimating a center position of a pupil in the eyeball on the basis of the information regarding the iris.

REFERENCE SIGNS LIST

1 Information processing system
10 Information processing device

101 Authentication processing unit
103 Pupil center estimation unit
105 Purkinje image position detection unit
107 Gaze estimation unit
109 Storage unit
20 Input and output device
201a, 201b First image capturing unit
203 Image capturing unit
203a, 203b Second image capturing unit
207 Operation unit
211 Output unit
291 Holding unit
293a, 293b Lens

The invention claimed is:

1. An information processing device, comprising:
a processing unit configured to:
acquire information that corresponds to an iris in an eyeball;
extract a partial image of a region of the iris based on the acquired information;
generate a first polar coordinate image based on a polar coordinate transformation of the extracted partial image; and
estimate a center position of a pupil in the eyeball based on the generated first polar coordinate image.

2. The information processing device according to claim 1, wherein
the processing unit is further configured to acquire an image of the eyeball as the information that corresponds to the iris, and
the image is captured by a camera.

3. The information processing device according to claim 1, wherein
the processing unit is further configured to generate the first polar coordinate image based on the polar coordinate transformation of the partial image around a point in the region,
the point corresponds to the pupil as a center to generate the first polar coordinate image.

4. The information processing device according to claim 1, wherein
the processing unit is further configured to estimate the center position of the pupil based on a comparison between the generated first polar coordinate image and a second polar coordinate image,
the second polar coordinate image is generated prior to the generation of the first polar coordinate image.

5. The information processing device according to claim 4, wherein the processing unit is further configured to estimate the center position of the pupil based on a comparison between the region of the iris in the first polar coordinate image and a region of the iris in the second polar coordinate image.

6. The information processing device according to claim 5, wherein the processing unit is further configured to:
sequentially change at least one of a plurality of conditions that corresponds to an area of the region of the iris from the first polar coordinate image; and
estimate the center position of the pupil based on a comparison between the region of the iris in the first polar coordinate image that corresponds to each of the plurality of conditions of the area, and the region of the iris in the second polar coordinate image.

7. The information processing device according to claim 5, wherein the processing unit is further configured to:
sequentially control a phase of the region of the iris in the first polar coordinate image in a direction that corresponds to angular coordinates in the polar coordinate transformation; and
estimate the center position of the pupil based on a comparison between the region of the iris in the first polar coordinate image with controlled phase, and the region of the iris in the second polar coordinate image.

8. The information processing device according to claim 4, wherein the processing unit is further configured to:
generate the first polar coordinate image for each of a plurality of points in the region that corresponds to the pupil; and
estimate the center position of the pupil based on a comparison between the first polar coordinate image that corresponds to each of the plurality of points, and the second polar coordinate image.

9. The information processing device according to claim 8, wherein
the processing unit is further configured to estimate that a point of a plurality of points matches the estimated center position of the pupil,
the point corresponds to the first polar coordinate image,
a difference of the point from the second polar coordinate image is smaller than a difference of each of a set of points other than the point, and
the plurality of points includes the set of points.

10. The information processing device according to claim 1, wherein the processing unit is further configured to:
integrate each pixel value of a plurality of pixel values of the first polar coordinate image in a direction that corresponds to radial coordinates in the polar coordinate transformation;
generate a first integral image based on the integration of each pixel value of the plurality of pixel values; and
estimate the center position of the pupil based the generated first integral image.

11. The information processing device according to claim 10, wherein
the processing unit is further configured to estimate the center position of the pupil based on a comparison between the generated first integral image and a second integral image, and
the second integral image is generated before the generation of the first integral image.

12. The information processing device according to claim 11, wherein the processing unit is further configured to estimate the center position of the pupil based on an integral value of a first pixel value of the plurality of pixel values in the region of the iris in the first integral image, and an integral value of a second pixel value of the plurality of pixel values in the region of the iris in the second integral image.

13. The information processing device according to claim 12, wherein
the processing unit is further configured to estimate the center position of the pupil based on a comparison between a first value of the first integral image and a second value of the second integral image,
the first value is obtained based on normalization of the integral value of the pixel value in a region of the first integral image that corresponds to a width of the region of the iris, and
the second value is obtained based on normalization of the integral value of the pixel value in a region of the second integral image that corresponds to a width of the region of the iris.

14. The information processing device according to claim 1, wherein
the region is in a substantially circular shape, and
the first polar coordinate image is in a substantially rectangular shape.

15. The information processing device according to claim 1, wherein the processing unit is further configured to estimate a direction of a gaze based on a result of the estimation of the center position of the pupil.

16. An information processing method, comprising:
acquiring information corresponding to an iris in an eyeball;
extracting a partial image of a region of the iris based on the acquired information;
generating a polar coordinate image based a polar coordinate transformation of the partial image; and
estimating a center position of a pupil in the eyeball based on the generated polar coordinate image.

17. A non-transitory computer-readable medium having stored thereon, computer-executable instructions which, when executed by a computer, cause the computer to execute operations, the operations comprising:
acquiring information corresponding to an iris in an eyeball;
extracting a partial image of a region of the iris based on the acquired information;
generating a polar coordinate image based on a polar coordinate transformation of the extracted partial image; and
estimating a center position of a pupil in the eyeball based on the generated polar coordinate image.

* * * * *